US007728121B2

(12) United States Patent
Simmonds et al.

(10) Patent No.: US 7,728,121 B2
(45) Date of Patent: Jun. 1, 2010

(54) HEPATITIS-C VIRUS TYPE 4, 5 AND 6

(75) Inventors: Peter Simmonds, Edinburgh (GB); Peng Lee Yap, Edinburgh (GB); Ian Hugo Pike, Tonbridge (GB)

(73) Assignee: Murex Diagnostics International, Inc., Bridgetown (BB)

( * ) Notice: Subject to any disclaimer, the term of this patent is extended or adjusted under 35 U.S.C. 154(b) by 0 days.

(21) Appl. No.: 11/933,672

(22) Filed: Nov. 1, 2007

(65) Prior Publication Data

US 2008/0262211 A1 Oct. 23, 2008

Related U.S. Application Data

(60) Division of application No. 11/676,842, filed on Feb. 20, 2007, now Pat. No. 7,402,315, which is a continuation of application No. 11/090,952, filed on Mar. 25, 2005, now Pat. No. 7,198,892, which is a division of application No. 08/537,802, filed as application No. PCT/GB94/00957 on May 5, 1994, now Pat. No. 6,881,821.

(30) Foreign Application Priority Data

May 5, 1993 (GB) ................................ 9309237.7
Jan. 7, 1994 (GB) ................................ 9400263.1

(51) Int. Cl.
*C07H 21/00* (2006.01)
*A61K 39/38* (2006.01)
*A61K 39/29* (2006.01)

(52) U.S. Cl. .................. 536/23.72; 536/23.1; 536/23.7; 424/184.1; 424/185.1; 424/189.1; 424/228.1

(58) Field of Classification Search ...................... None
See application file for complete search history.

(56) References Cited

U.S. PATENT DOCUMENTS 5,302,507 A 4/1994 Chiba et al.

FOREIGN PATENT DOCUMENTS

| | | | |
|---|---|---|---|
| DE | 42 09 215 | A1 | 3/1992 |
| EP | 0 318-216 | A1 | 5/1989 |
| EP | 0 518 313 | A2 | 12/1992 |
| WO | WO 94/25601 | | 11/1994 |
| WO | WO 95/11918 | | 5/1995 |

OTHER PUBLICATIONS

Simmonds et al., "Mapping of serotype-specific, immunodominant epitopes in the NS-4 region of hepatitis C virus (HCV): use of type-specific peptides to serologically differentiate infections with HCV types 1, 2, and 3," Journal of Clinical Microbiology, vol. 31 No. 6, pp. 1493-1503 (Jun. 1993).*

Cha, T.A., et al., "At Lease Five Related, But Distinct, Hepatitis C Viral Genotypes Exist," *Proc. Natl. Acad. Sci. USA*, Aug. 1, 1992, pp. 7144-7148, vol. 89, No. 15.

Chan, S. W., et al., "Analysis of a New Hepatitis C Virus Type and Its Phylogenetic Relationship to Existing Variants," *Journal of General Virology*, 1992, pp. 1131-1141, vol. 73.

Farci, P., et al., "Immunity Elicited by Hepatitis C. Virus," *Gastroenterology*, Apr. 1993, pp. 1228-1229, vol. 104, No. 4.

GenPept Accession ABC58484, "Non-Structural Protein 4b [Hepatitis C. Virus]," May 2006.

Huang, et al., "Recent Development of Therapeutics for Chronic HCV Infection," *Antiviral Research*, Sep. 2006, pp. 351-362, vol. 71, Nos. 2-3.

Leroux-Roels, "Development of Prophylactic and Therapeutic Vaccines Against Hepatitis C Virus," *Expert Review of Vaccines*, Jun. 2005, pp. 351-371, vol. 4, No. 3.

Marguerite, M., et al., "Analysis of Antigenicity and Immunogenicity of Five Different Chemically Defined Constructs of a Peptide," *Mol. Immunol.*, Jun. 1992, pp. 793-800, vol. 29, No. 6.

Prince, A.M., "Challenges for Development of Hepatitis C Virus Vaccines," *FEMS Microbiol. Rev.* , Jul. 1994, pp. 273-277, vol. 14, No. 3.

Simmonds, P., et al., "Sequence Variability in the 5' Non-coding Region of Hepatitis C Virus: Identification of a new Virus Type and Restrictions on Sequence Diversity," *Journal of General Virology*, 1993, pp. 661-668, vol. 74.

Simmonds, P., et al., "Classification of Hepatitis C Virus Into Six Major Genotypes and a Series of Subtypes by Phylogenetic Analysis of the NS-5 Region," *Journal of General Virology*, 1993, pp. 2391-2399, vol. 74.

Wintermeyer, et al., "Vaccines to Prevent Chronic Hepatitis C. Virus Infection: Current Experimental and Preclinical Developments," *Journal of Gastroenterology*, Jun. 2007, pp. 424-432, vol. 42, No. 6.

* cited by examiner

*Primary Examiner*—Zachariah Lucas
(74) *Attorney, Agent, or Firm*—Alston & Bird LLP

(57) ABSTRACT

The present invention relates to a polynucleic acid composition comprising or consisting of at least one polynucleic acid containing 8 or more contiguous nucleotides corresponding to a nucleotide sequence from the region spanning positions 417 to 957 of the Core/E1 region of HCV type 3; and/or the region spanning positions 4664 to 4730 of the NS3 region of HCV type 3; and/or the region spanning positions 4892 to 5292 of the NS3/4 region of HCV type 3; and/or the region spanning positions 8023 to 8235 of the NS5 region of the BR36 subgroup of HCV type 3a; and/or the coding region of HCV type 4a starting at nucleotide 379 in the core region; and/or the coding region of HCV type 4; and/or the coding region of HCV type 5, with said nucleotide numbering being with respect to the numbering of HCV nucleic acids as shown in Table 1, and with said polynucleic acids containing at least one nucleotide difference with known HCV type 1, and/or HCV type 2 genomes in the above-indicated regions, or the complement thereof.

1 Claim, 5 Drawing Sheets

FIG. 1

NS5 REGION

```
          2659                                                          2695

1a  12  I Y Q C C D L D P Q A R V_10 A I K_10 S L T E R L Y V G G P L T N S R G E N C G
                                 T_1      R_2
                                 M_1
4a  3   V . . . . N_1 . E . _2 E . . K  V_2 . T_2 A . . . . . _2 . _2 . _2 . . . M H . . K . D L . .
                  S_1    L_1          . _1  A_1            H_1 N_1 E_1
                  . _1
6a  1   . . . S . Q . . . V . . R  . V S  . . . . . . . . . . . . M V . . K . Q S . .


          2696                                                           2732

1a  12  Y R R C R A S G_11 V L T T_11 S C G N T L T C_11 Y I K A R_9 A A C R A A G L_11 Q_8 D C T
                        R_1       I_1                 R_1         Q_3               V_1 R_4
4a  3   . . . . . . . . . F_1 . . . F . . . . . . . L . . . T_2 . . I . . . . . . R_2 . . _2 .
                          Y_1                                 D_1                     K_1  S_1
6a  2   . . . . . . . . . . P . . M . . . I . . . L . . . H . - . . . . . N I K . . D
```

Type 4      NS5 REGION

```
EG7    GTCTATCAGTGTTGTGACCTGGAGCCCGAAGCCCGCAAGGTTATTGCTGCCCTCACAGAAAGACACAAT
EG13   GTCTATCAGTGTTGTAACCTGGAGCCCGAAGCTCGCAAGGCTATTACTGCCCTCACAGAAAGACTCTAC
EG19   GTCTATCAGTGTTGTAGTCTGGAGCTCGAGGCTCGCAAGGTTATTACTGCCCTCACGGAAAGACTCTAC

EG7    GAGGGCGGCCCCATGCACAACAGCAA........................................
EG13   GTGGGCGGCCCCATGCACAACAGCAAGGGAGACCTTTGTGGGTATCGGAGATGTCGGGCAAGCGGAGTC
EG19   GTGGGCGGCCCCATGCACAATAGCAAGGGAGACCTTTGTGGGTACCGGAGATGCCGGGCAAGCGGAGTC

EG7    ................CCACACTGACGTGCTATCTCAAAGCCGACGCCGCTATCAGAGCGGCAGGC
EG13   TTTACGACCAGCTTCGGAAACACGCTGACGTGCTACCTAAAAGCCACGGCCGCTATTAGAGCGGCGGGG
EG19   TATACGACCAGCTTCGGAAACACGCTGACGTGCTACCTCAAAGCCACAGCCGCTATTAGGGCGGCGGGA

EG7    CTGAGAGACTGCACC
EG13   CTGAGAGACTGCACT
EG19   CTAAAAGACAGCACT
```

Type 6

```
HK2    ATCTATCAGTCTTGCCAGCTGGATCCCGTAGCAAGGAGGGCAGTATCATCCCTGACAGAACGGCTCTAC

HK2    GTAGGCGGCCCCATGGTGAACTCCAAGGGACAGTCATGTGGCTACCGTAGATGCCGCGCCAGTGGGGTG

HK2    CTGCCCACGAGCATGGGAAACACCATCACGTGCTATCTGAAGGCACACGCC---TGCAGGGCGGCCAAC

HK2    ATCAAGGACTGTGAC
```

Sequences shown correspond to positions 7975 to 8196 in Choo et al., (1991)
"." : Sequence not determined
"-" : Gap introduced into sequence to preserve alignment

FIG. 4

PCR primers Legend: +, sense; -, antisense; O, outer; I, inner.

| | | | |
|---|---|---|---|
| 007 | AACTCGAGTATCCCACTGATGAAGTTCCACAT | O | - |
| 435 | CACCCATCACCAAATACAT | O | + |
| 5351 | TTTTGGATCCATGCATGTCAGCTGATCTGG | I | + |
| 5943 | TTTTGGATCCACATGTGCTTCGCCCAGAA | I | - |

Primers 253, 281 and 221 are described in Simmonds *et al.*, 1993, *J. Clin. Microb.* 31: 1493.

FIG. 5

| TYPE | NS4 REGION 1 | | | |
|---|---|---|---|---|
| 1 | AAGCCGGCT | GTC/ATT | ATTCCCGACAGGGAAGTTCTCTACCAGGAGTTCGATGAAATG | 54 |
| | K P A | V / I | I P D R E V L Y Q E F D E M | 18 |
| 2 | CGAGTGGTC | GTGA | CTCCGGACAAGGAGGTCCTCTATGAGGCTTTTGACGAGATG | 54 |
| | R V V | V | T P D K E V L Y E A F D E M | 18 |
| 3 | AAGCCGGCA | TTG | GTTCCAGACAAAGAGGTGTTGTATCAACAATACGATGAGATG | 54 |
| | K P A | L | V P D K E V L Y Q Q Y D E M | 18 |
| 4 | CAGCCTGCT | GTT | ATCCCTGACCGCGAGGTGCTCTACCAGCAGTTCGACGAAATG | 54 |
| | Q P A | V | I P D R E V L Y Q Q F D E M | 18 |
| 5 | AGACCTGCC | ATC | ATTCCCGATAGAGAGGTGTTGTACCAGCAATTTGATAAGATG | 54 |
| | R P A | I | I P D R E V L Y Q Q F D K M | 18 |
| 6 | AAGCCTGCT | GTT | GTCCCTGATCGCGAGATCTTATACCAGCAGTTTGACGAGATG | 54 |
| | K P A | V | V P D R E I L Y Q Q F D E M | 18 |

| TYPE | NS4 REGION 2 | | | |
|---|---|---|---|---|
| 1 | GAGTGCGCCTCACACCTCCCTTACATCGAGCAGGGA | ATG/GCC | CAGCTCGCCGAG | CAATTC |
| | E C A S H L P Y I E Q G | M / A | Q L A E | Q F |
| 2 | GAATGTGCCTCTAGAGCGGCCCTCATTGAAGAGGGG | CAG | CGGATAGCCGAG | ATGCTG |
| | E C A S R A A L I E E G | Q | R I A E | M L |
| 3 | GAGTGCTCGCAAGCTGCCCCATATATCGAACAAGCT | CAG | GTGATAGCCCAC | CAGTTC |
| | E C S Q A A P Y I E Q A | Q | V I A H | Q F |
| 4 | GAGTGTTCCAAACACCTTCCACTAGTCGAGCACGGG | TTG | CAACTTGCTGAG | CAATTC |
| | E C S K H L P L V E H G | L | Q L A S | Q F |
| 5 | GAGTGCTCGACCTCGCTCCCCTATATGGACGAGGCA | CGT | GCTATTGCCGGG | CAATTC |
| | E C S T S L P Y M D E A | R | A I A G | Q F |
| 6 | GAGTGCTCTAGGCACATCCCCTACCTCGCTGAGGGC | CAG | CAGATCGCCGAA | CAGTTC |
| | E C S R H I P Y L A E G | Q | Q I A E | Q F |

SEQUENCE LISTING

```
<160> NUMBER OF SEQ ID NOS: 58

<210> SEQ ID NO 1
<211> LENGTH: 74
<212> TYPE: PRT
<213> ORGANISM: Hepatitis C Virus
<220> FEATURE:
<221> NAME/KEY: VARIANT
<222> LOCATION: (0)...(0)
<223> OTHER INFORMATION: HCV 1A NS5 REGION; ISOLATE PT-1

<400> SEQUENCE: 1

Ile Tyr Gln Cys Cys Asp Leu Asp Pro Gln Ala Arg Val Ala Ile Lys
 1               5                  10                  15

Ser Leu Thr Glu Arg Leu Tyr Val Gly Gly Pro Leu Thr Asn Ser Arg
            20                  25                  30

Gly Glu Asn Cys Gly Tyr Arg Arg Cys Arg Ala Ser Gly Val Leu Thr
        35                  40                  45

Thr Ser Cys Gly Asn Thr Leu Thr Cys Tyr Ile Lys Ala Arg Ala Ala
    50                  55                  60

Cys Arg Ala Ala Gly Leu Arg Asp Cys Thr
65                  70
```

-continued

```
<210> SEQ ID NO 2
<211> LENGTH: 74
<212> TYPE: PRT
<213> ORGANISM: Hepatitis C Virus
<220> FEATURE:
<221> NAME/KEY: VARIANT
<222> LOCATION: (0)...(0)
<223> OTHER INFORMATION: HCV 1A NS5 REGION; ISOLATE GM2

<400> SEQUENCE: 2

Ile Tyr Gln Cys Cys Asp Leu Asp Pro Gln Ala Arg Val Ala Ile Lys
 1              5                   10                  15

Ser Leu Thr Glu Arg Leu Tyr Val Gly Gly Pro Leu Thr Asn Ser Arg
            20                  25                  30

Gly Glu Asn Cys Gly Tyr Arg Arg Cys Arg Ala Ser Gly Val Leu Thr
        35                  40                  45

Thr Ser Cys Gly Asn Thr Leu Thr Cys Tyr Ile Lys Ala Arg Ala Ala
    50                  55                  60

Cys Arg Ala Ala Gly Leu Gln Asp Cys Thr
65                  70


<210> SEQ ID NO 3
<211> LENGTH: 74
<212> TYPE: PRT
<213> ORGANISM: Hepatitis C Virus
<220> FEATURE:
<221> NAME/KEY: VARIANT
<222> LOCATION: (0)...(0)
<223> OTHER INFORMATION: HCV 1A NS5 REGION; ISOLATE H90

<400> SEQUENCE: 3

Ile Tyr Gln Cys Cys Asp Leu Asp Pro Gln Ala Arg Thr Ala Ile Lys
 1              5                   10                  15

Ser Leu Thr Glu Arg Leu Tyr Val Gly Gly Pro Leu Thr Asn Ser Arg
            20                  25                  30

Gly Glu Asn Cys Gly Tyr Arg Arg Cys Arg Ala Ser Gly Val Leu Thr
        35                  40                  45

Thr Ser Cys Gly Asn Thr Leu Thr Cys Tyr Ile Lys Ala Arg Ala Ala
    50                  55                  60

Cys Arg Ala Ala Gly Leu Gln Asp Cys Thr
65                  70


<210> SEQ ID NO 4
<211> LENGTH: 74
<212> TYPE: PRT
<213> ORGANISM: Hepatitis C Virus
<220> FEATURE:
<221> NAME/KEY: VARIANT
<222> LOCATION: (0)...(0)
<223> OTHER INFORMATION: HCV 1A NS5 REGION; ISOLATE 1801

<400> SEQUENCE: 4

Ile Tyr Gln Cys Cys Asp Leu Asp Pro Gln Ala Arg Val Ala Ile Arg
 1              5                   10                  15

Ser Leu Thr Glu Arg Leu Tyr Val Gly Gly Pro Leu Thr Asn Ser Arg
            20                  25                  30

Gly Glu Asn Cys Gly Tyr Arg Arg Cys Arg Ala Ser Gly Val Leu Thr
        35                  40                  45

Ile Ser Cys Gly Asn Thr Leu Thr Cys Tyr Ile Lys Ala Arg Ala Ala
    50                  55                  60

Cys Arg Ala Ala Gly Val Arg Asp Cys Thr
65                  70
```

-continued

<210> SEQ ID NO 5
<211> LENGTH: 74
<212> TYPE: PRT
<213> ORGANISM: Hepatitis C Virus
<220> FEATURE:
<221> NAME/KEY: VARIANT
<222> LOCATION: (0)...(0)
<223> OTHER INFORMATION: HCV 1A NS5 REGION; ISOLATE 1825

<400> SEQUENCE: 5

```
Ile Tyr Gln Cys Cys Asp Leu Asp Pro Gln Ala Arg Val Ala Ile Arg
 1               5                  10                  15

Ser Leu Thr Glu Arg Leu Tyr Val Gly Gly Pro Leu Thr Asn Ser Arg
            20                  25                  30

Gly Glu Asn Cys Gly Tyr Arg Arg Cys Arg Ala Ser Gly Val Leu Thr
        35                  40                  45

Thr Ser Cys Gly Asn Thr Leu Thr Cys Tyr Ile Lys Ala Gln Ala Ala
    50                  55                  60

Cys Arg Ala Ala Gly Leu Arg Asp Cys Thr
65                  70
```

<210> SEQ ID NO 6
<211> LENGTH: 74
<212> TYPE: PRT
<213> ORGANISM: Hepatitis C Virus
<220> FEATURE:
<221> NAME/KEY: VARIANT
<222> LOCATION: (0)...(0)
<223> OTHER INFORMATION: HCV 1A NS5 REGION; ISOLATE 2138

<400> SEQUENCE: 6

```
Ile Tyr Gln Cys Cys Asp Leu Asp Pro Gln Ala Arg Val Ala Ile Lys
 1               5                  10                  15

Ser Leu Thr Glu Arg Leu Tyr Val Gly Gly Pro Leu Thr Asn Ser Arg
            20                  25                  30

Gly Glu Asn Cys Gly Tyr Arg Arg Cys Arg Ala Ser Gly Val Leu Thr
        35                  40                  45

Thr Ser Cys Gly Asn Thr Leu Thr Cys Tyr Ile Lys Ala Gln Ala Ala
    50                  55                  60

Cys Arg Ala Ala Gly Leu Gln Asp Cys Thr
65                  70
```

<210> SEQ ID NO 7
<211> LENGTH: 74
<212> TYPE: PRT
<213> ORGANISM: Hepatitis C Virus
<220> FEATURE:
<221> NAME/KEY: VARIANT
<222> LOCATION: (0)...(0)
<223> OTHER INFORMATION: HCV 1A NS5 REGION; ISOLATE 121

<400> SEQUENCE: 7

```
Ile Tyr Gln Cys Cys Asp Leu Asp Pro Gln Ala Arg Met Ala Ile Lys
 1               5                  10                  15

Ser Leu Thr Glu Arg Leu Tyr Val Gly Gly Pro Leu Thr Asn Ser Arg
            20                  25                  30

Gly Glu Asn Cys Gly Tyr Arg Arg Cys Arg Ala Ser Gly Val Leu Thr
        35                  40                  45

Thr Ser Cys Gly Asn Thr Leu Thr Cys Tyr Ile Lys Ala Arg Ala Ala
    50                  55                  60
```

-continued

```
Cys Arg Ala Ala Gly Leu Gln Asp Cys Thr
65                  70


<210> SEQ ID NO 8
<211> LENGTH: 74
<212> TYPE: PRT
<213> ORGANISM: Hepatitis C Virus
<220> FEATURE:
<221> NAME/KEY: VARIANT
<222> LOCATION: (0)...(0)
<223> OTHER INFORMATION: HCV 1A NS5 REGION; ISOLATE us17

<400> SEQUENCE: 8

Ile Tyr Gln Cys Cys Asp Leu Asp Pro Gln Ala Arg Val Ala Ile Lys
 1               5                  10                  15

Ser Leu Thr Glu Arg Leu Tyr Val Gly Gly Pro Leu Thr Asn Ser Arg
            20                  25                  30

Gly Glu Asn Cys Gly Tyr Arg Arg Cys Arg Ala Ser Gly Val Leu Thr
        35                  40                  45

Thr Ser Cys Gly Asn Thr Leu Thr Cys Tyr Ile Lys Ala Gln Ala Ala
    50                  55                  60

Cys Arg Ala Ala Gly Leu Arg Asp Cys Thr
65                  70


<210> SEQ ID NO 9
<211> LENGTH: 74
<212> TYPE: PRT
<213> ORGANISM: Hepatitis C Virus
<220> FEATURE:
<221> NAME/KEY: VARIANT
<222> LOCATION: (0)...(0)
<223> OTHER INFORMATION: HCV 1A NS5 REGION; ISOLATE H

<400> SEQUENCE: 9

Ile Tyr Gln Cys Cys Asp Leu Asp Pro Gln Ala Arg Val Ala Ile Lys
 1               5                  10                  15

Ser Leu Thr Glu Arg Leu Tyr Val Gly Gly Pro Leu Thr Asn Ser Arg
            20                  25                  30

Gly Glu Asn Cys Gly Tyr Arg Arg Cys Arg Ala Ser Arg Val Leu Thr
        35                  40                  45

Thr Ser Cys Gly Asn Thr Leu Thr Arg Tyr Ile Lys Ala Arg Ala Ala
    50                  55                  60

Cys Arg Ala Ala Gly Leu Gln Asp Cys Thr
65                  70


<210> SEQ ID NO 10
<211> LENGTH: 222
<212> TYPE: DNA
<213> ORGANISM: Hepatitis C Virus
<220> FEATURE:
<221> NAME/KEY: misc_feature
<222> LOCATION: (0)...(0)
<223> OTHER INFORMATION: HCV 1A NS5; ISOLATE EG7
<220> FEATURE:
<221> NAME/KEY: CDS
<222> LOCATION: (1)...(95)
<220> FEATURE:
<221> NAME/KEY: CDS
<222> LOCATION: (160)...(222)
<220> FEATURE:
<221> NAME/KEY: misc_feature
<222> LOCATION: 96, 97, 98, 99, 100, 101, 102, 103, 104, 105, 106, 107,
      108, 109, 110, 111, 112, 113, 114, 115, 116, 117, 118, 119, 120,
      121, 122, 123, 124, 125, 126, 127, 128, 129, 130, 131, 132,
      133, 134, 135, 136, 137, 138, 139, 140, 141, 142
<223> OTHER INFORMATION: n = A,T,C or G
```

-continued

```
<220> FEATURE:
<221> NAME/KEY: misc_feature
<222> LOCATION: 143, 144, 145, 146, 147, 148, 149, 150, 151, 152, 153,
      154, 155, 156, 157
<223> OTHER INFORMATION: n = A,T,C or G

<400> SEQUENCE: 10

gtc tat cag tgt tgt gac ctg gag ccc gaa gcc cgc aag gtt att gct       48
Val Tyr Gln Cys Cys Asp Leu Glu Pro Glu Ala Arg Lys Val Ile Ala
 1               5                  10                  15

gcc ctc aca gaa aga cac aat gag ggc ggc ccc atg cac aac agc aa        95
Ala Leu Thr Glu Arg His Asn Glu Gly Gly Pro Met His Asn Ser
             20                  25                  30

nnnnnnnnnn nnnnnnnnnn nnnnnnnnnn nnnnnnnnnn nnnnnnnnnn nnnnnnnnnn    155

nnc c aca ctg acg tgc tat ctc aaa gcc gac gcc gct atc aga gcg gca    204
      Thr Leu Thr Cys Tyr Leu Lys Ala Asp Ala Ala Ile Arg Ala Ala
               35                  40                  45

ggc ctg aga gac tgc acc                                              222
Gly Leu Arg Asp Cys Thr
         50


<210> SEQ ID NO 11
<211> LENGTH: 31
<212> TYPE: PRT
<213> ORGANISM: Hepatitis C Virus

<400> SEQUENCE: 11

Val Tyr Gln Cys Cys Asp Leu Glu Pro Glu Ala Arg Lys Val Ile Ala
 1               5                  10                  15

Ala Leu Thr Glu Arg His Asn Glu Gly Gly Pro Met His Asn Ser
            20                  25                  30


<210> SEQ ID NO 12
<211> LENGTH: 21
<212> TYPE: PRT
<213> ORGANISM: Hepatitis C Virus

<400> SEQUENCE: 12

Thr Leu Thr Cys Tyr Leu Lys Ala Asp Ala Ala Ile Arg Ala Ala Gly
 1               5                  10                  15

Leu Arg Asp Cys Thr
            20


<210> SEQ ID NO 13
<211> LENGTH: 222
<212> TYPE: DNA
<213> ORGANISM: Hepatitis C Virus
<220> FEATURE:
<221> NAME/KEY: misc_feature
<222> LOCATION: (0)...(0)
<223> OTHER INFORMATION: HCV 4A NS5 REGION; ISOLATE EG13
<220> FEATURE:
<221> NAME/KEY: CDS
<222> LOCATION: (1)...(222)

<400> SEQUENCE: 13

gtc tat cag tgt tgt aac ctg gag ccc gaa gct cgc aag gct att act       48
Val Tyr Gln Cys Cys Asn Leu Glu Pro Glu Ala Arg Lys Ala Ile Thr
 1               5                  10                  15

gcc ctc aca gaa aga ctc tac gtg ggc ggc ccc atg cac aac agc aag       96
Ala Leu Thr Glu Arg Leu Tyr Val Gly Gly Pro Met His Asn Ser Lys
             20                  25                  30

gga gac ctt tgt ggg tat cgg aga tgt cgg gca agc gga gtc ttt acg      144
Gly Asp Leu Cys Gly Tyr Arg Arg Cys Arg Ala Ser Gly Val Phe Thr
```

-continued

```
        35                  40                  45

acc agc ttc gga aac acg ctg acg tgc tac cta aaa gcc acg gcc gct      192
Thr Ser Phe Gly Asn Thr Leu Thr Cys Tyr Leu Lys Ala Thr Ala Ala
     50                  55                  60

att aga gcg gcg ggg ctg aga gac tgc act                              222
Ile Arg Ala Ala Gly Leu Arg Asp Cys Thr
 65                  70
```

<210> SEQ ID NO 14
<211> LENGTH: 74
<212> TYPE: PRT
<213> ORGANISM: Hepatitis C Virus

<400> SEQUENCE: 14

```
Val Tyr Gln Cys Cys Asn Leu Glu Pro Glu Ala Arg Lys Ala Ile Thr
 1               5                  10                  15

Ala Leu Thr Glu Arg Leu Tyr Val Gly Gly Pro Met His Asn Ser Lys
            20                  25                  30

Gly Asp Leu Cys Gly Tyr Arg Arg Cys Arg Ala Ser Gly Val Phe Thr
        35                  40                  45

Thr Ser Phe Gly Asn Thr Leu Thr Cys Tyr Leu Lys Ala Thr Ala Ala
    50                  55                  60

Ile Arg Ala Ala Gly Leu Arg Asp Cys Thr
65                  70
```

<210> SEQ ID NO 15
<211> LENGTH: 222
<212> TYPE: DNA
<213> ORGANISM: Hepatitis C Virus
<220> FEATURE:
<221> NAME/KEY: misc_feature
<222> LOCATION: (0)...(0)
<223> OTHER INFORMATION: HCV 4A NS5 REGION; ISOLATE EG19
<220> FEATURE:
<221> NAME/KEY: CDS
<222> LOCATION: (1)...(222)

<400> SEQUENCE: 15

```
gtc tat cag tgt tgt agt ctg gag ctc gag gct cgc aag gtt att act       48
Val Tyr Gln Cys Cys Ser Leu Glu Leu Glu Ala Arg Lys Val Ile Thr
 1               5                  10                  15

gcc ctc acg gaa aga ctc tac gtg ggc ggc ccc atg cac aat agc aag       96
Ala Leu Thr Glu Arg Leu Tyr Val Gly Gly Pro Met His Asn Ser Lys
            20                  25                  30

gga gac ctt tgt ggg tac cgg aga tgc cgg gca agc gga gtc tat acg      144
Gly Asp Leu Cys Gly Tyr Arg Arg Cys Arg Ala Ser Gly Val Tyr Thr
        35                  40                  45

acc agc ttc gga aac acg ctg acg tgc tac ctc aaa gcc aca gcc gct      192
Thr Ser Phe Gly Asn Thr Leu Thr Cys Tyr Leu Lys Ala Thr Ala Ala
     50                  55                  60

att agg gcg gcg gga cta aaa gac agc act                              222
Ile Arg Ala Ala Gly Leu Lys Asp Ser Thr
 65                  70
```

<210> SEQ ID NO 16
<211> LENGTH: 74
<212> TYPE: PRT
<213> ORGANISM: Hepatitis C Virus

<400> SEQUENCE: 16

```
Val Tyr Gln Cys Cys Ser Leu Glu Leu Glu Ala Arg Lys Val Ile Thr
 1               5                  10                  15
```

-continued

```
Ala Leu Thr Glu Arg Leu Tyr Val Gly Gly Pro Met His Asn Ser Lys
            20                  25                  30

Gly Asp Leu Cys Gly Tyr Arg Arg Cys Arg Ala Ser Gly Val Tyr Thr
        35                  40                  45

Thr Ser Phe Gly Asn Thr Leu Thr Cys Tyr Leu Lys Ala Thr Ala Ala
    50                  55                  60

Ile Arg Ala Ala Gly Leu Lys Asp Ser Thr
65                  70


<210> SEQ ID NO 17
<211> LENGTH: 219
<212> TYPE: DNA
<213> ORGANISM: Hepatitis C Virus
<220> FEATURE:
<221> NAME/KEY: CDS
<222> LOCATION: (1)...(219)
<220> FEATURE:
<221> NAME/KEY: misc_feature
<222> LOCATION: (0)...(0)
<223> OTHER INFORMATION: HCV 6A NS5 REGION; ISOLATE HK2

<400> SEQUENCE: 17

atc tat cag tct tgc cag ctg gat ccc gta gca agg agg gca gta tca       48
Ile Tyr Gln Ser Cys Gln Leu Asp Pro Val Ala Arg Arg Ala Val Ser
 1               5                  10                  15

tcc ctg aca gaa cgg ctc tac gta ggc ggc ccc atg gtg aac tcc aag       96
Ser Leu Thr Glu Arg Leu Tyr Val Gly Gly Pro Met Val Asn Ser Lys
             20                  25                  30

gga cag tca tgt ggc tac cgt aga tgc cgc gcc agt ggg gtg ctg ccc      144
Gly Gln Ser Cys Gly Tyr Arg Arg Cys Arg Ala Ser Gly Val Leu Pro
         35                  40                  45

acg agc atg gga aac acc atc acg tgc tat ctg aag gca cac gcc tgc      192
Thr Ser Met Gly Asn Thr Ile Thr Cys Tyr Leu Lys Ala His Ala Cys
     50                  55                  60

agg gcg gcc aac atc aag gac tgt gac                                  219
Arg Ala Ala Asn Ile Lys Asp Cys Asp
 65                  70


<210> SEQ ID NO 18
<211> LENGTH: 73
<212> TYPE: PRT
<213> ORGANISM: Hepatitis C Virus

<400> SEQUENCE: 18

Ile Tyr Gly Ser Cys Gln Leu Asp Pro Val Ala Arg Arg Ala Val Ser
 1               5                  10                  15

Ser Leu Thr Glu Arg Leu Tyr Val Gly Gly Pro Met Val Asn Ser Lys
            20                  25                  30

Gly Gln Ser Cys Gly Tyr Arg Arg Cys Arg Ala Ser Gly Val Leu Pro
        35                  40                  45

Thr Ser Met Gly Asn Thr Ile Thr Cys Tyr Leu Lys Ala His Ala Cys
    50                  55                  60

Arg Ala Ala Asn Ile Lys Asp Cys Asp
65                  70


<210> SEQ ID NO 19
<211> LENGTH: 32
<212> TYPE: DNA
<213> ORGANISM: Artificial Sequence
<220> FEATURE:
<223> OTHER INFORMATION: Anti-sense Primer 007

<400> SEQUENCE: 19
```

-continued

```
aactcgagta tcccactgat gaagttccac at                                   32


<210> SEQ ID NO 20
<211> LENGTH: 19
<212> TYPE: DNA
<213> ORGANISM: Artificial Sequence
<220> FEATURE:
<223> OTHER INFORMATION: Sense Primer 435

<400> SEQUENCE: 20

cacccatcac caaatacat                                                  19


<210> SEQ ID NO 21
<211> LENGTH: 30
<212> TYPE: DNA
<213> ORGANISM: Artificial Sequence
<220> FEATURE:
<223> OTHER INFORMATION: Sense Primer 5351

<400> SEQUENCE: 21

ttttggatcc atgcatgtca gctgatctgg                                      30


<210> SEQ ID NO 22
<211> LENGTH: 29
<212> TYPE: DNA
<213> ORGANISM: Artificial Sequence
<220> FEATURE:
<223> OTHER INFORMATION: Antisense Primer 5943

<400> SEQUENCE: 22

ttttggatcc acatgtgctt cgcccagaa                                       29


<210> SEQ ID NO 23
<211> LENGTH: 54
<212> TYPE: DNA
<213> ORGANISM: Hepatitis C Virus
<220> FEATURE:
<221> NAME/KEY: CDS
<222> LOCATION: (1)...(54)
<220> FEATURE:
<221> NAME/KEY: misc_feature
<222> LOCATION: (0)...(0)
<223> OTHER INFORMATION: HCV TYPE 1 NS4 REGION 1

<400> SEQUENCE: 23

aag ccg gct gtc att ccc gac agg gaa gtt ctc tac cag gag ttc gat       48
Lys Pro Ala Val Ile Pro Asp Arg Glu Val Leu Tyr Gln Glu Phe Asp
 1               5                  10                  15

gaa atg                                                               54
Glu Met


<210> SEQ ID NO 24
<211> LENGTH: 18
<212> TYPE: PRT
<213> ORGANISM: Hepatitis C Virus

<400> SEQUENCE: 24

Lys Pro Ala Val Ile Pro Asp Arg Glu Val Leu Tyr Gln Glu Phe Asp
 1               5                  10                  15

Glu Met


<210> SEQ ID NO 25
<211> LENGTH: 54
<212> TYPE: DNA
<213> ORGANISM: Hepatitis C Virus
```

-continued

```
<220> FEATURE:
<221> NAME/KEY: CDS
<222> LOCATION: (1)...(54)
<220> FEATURE:
<221> NAME/KEY: misc_feature
<222> LOCATION: (0)...(0)
<223> OTHER INFORMATION: HCV TYPE 1 NS4 REGION 1

<400> SEQUENCE: 25

aag ccg gct att att ccc gac agg gaa gtt ctc tac cag gag ttc gat       48
Lys Pro Ala Ile Ile Pro Asp Arg Glu Val Leu Tyr Gln Glu Phe Asp
 1               5                   10                  15

gaa atg                                                               54
Glu Met


<210> SEQ ID NO 26
<211> LENGTH: 18
<212> TYPE: PRT
<213> ORGANISM: Hepatitis C Virus

<400> SEQUENCE: 26

Lys Pro Ala Ile Ile Pro Asp Arg Glu Val Leu Tyr Gln Glu Phe Asp
 1               5                  10                  15

Glu Met


<210> SEQ ID NO 27
<211> LENGTH: 54
<212> TYPE: DNA
<213> ORGANISM: Hepatitis C Virus
<220> FEATURE:
<221> NAME/KEY: CDS
<222> LOCATION: (1)...(54)
<220> FEATURE:
<221> NAME/KEY: misc_feature
<222> LOCATION: (0)...(0)
<223> OTHER INFORMATION: HCV TYPE 2 NS4 REGION 1

<400> SEQUENCE: 27

cga gtg gtc gtg act ccg gac aag gag gtc ctc tat gag gct ttt gac       48
Arg Val Val Val Thr Pro Asp Lys Glu Val Leu Tyr Glu Ala Phe Asp
 1               5                   10                  15

gag atg                                                               54
Glu Met


<210> SEQ ID NO 28
<211> LENGTH: 18
<212> TYPE: PRT
<213> ORGANISM: Hepatitis C Virus

<400> SEQUENCE: 28

Arg Val Val Val Thr Pro Asp Lys Glu Val Leu Tyr Glu Ala Phe Asp
 1               5                  10                  15

Glu Met


<210> SEQ ID NO 29
<211> LENGTH: 54
<212> TYPE: DNA
<213> ORGANISM: Hepatitis C Virus
<220> FEATURE:
<221> NAME/KEY: CDS
<222> LOCATION: (1)...(54)
<220> FEATURE:
<221> NAME/KEY: misc_feature
<222> LOCATION: (0)...(0)
<223> OTHER INFORMATION: HCV TYPE 3 NS4 REGION 1

<400> SEQUENCE: 29
```

-continued

```
aag ccg gca ttg gtt cca gac aaa gag gtg ttg tat caa caa tac gat       48
Lys Pro Ala Leu Val Pro Asp Lys Glu Val Leu Tyr Gln Gln Tyr Asp
 1               5                  10                  15

gag atg                                                               54
Glu Met


<210> SEQ ID NO 30
<211> LENGTH: 18
<212> TYPE: PRT
<213> ORGANISM: Hepatitis C Virus

<400> SEQUENCE: 30

Lys Pro Ala Leu Val Pro Asp Lys Glu Val Leu Tyr Gln Gln Tyr Asp
 1               5                  10                  15

Glu Met


<210> SEQ ID NO 31
<211> LENGTH: 54
<212> TYPE: DNA
<213> ORGANISM: Hepatitis C Virus
<220> FEATURE:
<221> NAME/KEY: CDS
<222> LOCATION: (1)...(54)
<220> FEATURE:
<221> NAME/KEY: misc_feature
<222> LOCATION: (0)...(0)
<223> OTHER INFORMATION: HCV TYPE 4 NS4 REGION 1

<400> SEQUENCE: 31

cag cct gct gtt atc cct gac cgc gag gtg ctc tac cag cag ttc gac       48
Gln Pro Ala Val Ile Pro Asp Arg Glu Val Leu Tyr Gln Gln Phe Asp
 1               5                  10                  15

gaa atg                                                               54
Glu Met


<210> SEQ ID NO 32
<211> LENGTH: 18
<212> TYPE: PRT
<213> ORGANISM: Hepatitis C Virus

<400> SEQUENCE: 32

Gln Pro Ala Val Ile Pro Asp Arg Glu Val Leu Tyr Gln Gln Phe Asp
 1               5                  10                  15

Glu Met


<210> SEQ ID NO 33
<211> LENGTH: 54
<212> TYPE: DNA
<213> ORGANISM: Hepatitis C Virus
<220> FEATURE:
<221> NAME/KEY: CDS
<222> LOCATION: (1)...(54)
<220> FEATURE:
<221> NAME/KEY: misc_feature
<222> LOCATION: (0)...(0)
<223> OTHER INFORMATION: HCV TYPE 5 NS4 REGION 1

<400> SEQUENCE: 33

aga cct gcc atc att ccc gat aga gag gtg ttg tac cag caa ttt gat       48
Arg Pro Ala Ile Ile Pro Asp Arg Glu Val Leu Tyr Gln Gln Phe Asp
 1               5                  10                  15

aag atg                                                               54
Lys Met
```

-continued

<210> SEQ ID NO 34
<211> LENGTH: 18
<212> TYPE: PRT
<213> ORGANISM: Hepatitis C Virus

<400> SEQUENCE: 34

Arg Pro Ala Ile Ile Pro Asp Arg Glu Val Leu Tyr Gln Gln Phe Asp
 1               5                  10                  15

Lys Met

<210> SEQ ID NO 35
<211> LENGTH: 54
<212> TYPE: DNA
<213> ORGANISM: Hepatitis C Virus
<220> FEATURE:
<221> NAME/KEY: CDS
<222> LOCATION: (1)...(54)
<220> FEATURE:
<221> NAME/KEY: misc_feature
<222> LOCATION: (0)...(0)
<223> OTHER INFORMATION: HCV TYPE 6 NS4 REGION 1

<400> SEQUENCE: 35 aag cct gct gtt gtc cct gat cgc gag atc tta tac cag cag ttt gac       48
Lys Pro Ala Val Val Pro Asp Arg Glu Ile Leu Tyr Gln Gln Phe Asp
 1               5                  10                  15 gag atg                                                               54
Glu Met <210> SEQ ID NO 36
<211> LENGTH: 18
<212> TYPE: PRT
<213> ORGANISM: Hepatitis C Virus

<400> SEQUENCE: 36

Lys Pro Ala Val Val Pro Asp Arg Glu Ile Leu Tyr Gln Gln Phe Asp
 1               5                  10                  15

Glu Met

<210> SEQ ID NO 37
<211> LENGTH: 57
<212> TYPE: DNA
<213> ORGANISM: Hepatitis C Virus
<220> FEATURE:
<221> NAME/KEY: CDS
<222> LOCATION: (1)...(57)
<220> FEATURE:
<221> NAME/KEY: misc_feature
<222> LOCATION: (0)...(0)
<223> OTHER INFORMATION: HCV TYPE 1 NS4 REGION 2

<400> SEQUENCE: 37 gag tgc gcc tca cac ctc cct tac atc gag cag gga atg cag ctc gcc       48
Glu Cys Ala Ser His Leu Pro Tyr Ile Glu Gln Gly Met Gln Leu Ala
 1               5                  10                  15 gag caa ttc                                                           57
Glu Gln Phe <210> SEQ ID NO 38
<211> LENGTH: 19
<212> TYPE: PRT
<213> ORGANISM: Hepatitis C Virus

<400> SEQUENCE: 38

Glu Cys Ala Ser His Leu Pro Tyr Ile Glu Gln Gly Met Gln Leu Ala
 1               5                  10                  15

-continued

```
Glu Gln Phe


<210> SEQ ID NO 39
<211> LENGTH: 57
<212> TYPE: DNA
<213> ORGANISM: Hepatitis C Virus
<220> FEATURE:
<221> NAME/KEY: CDS
<222> LOCATION: (1)...(57)
<220> FEATURE:
<221> NAME/KEY: misc_feature
<222> LOCATION: (0)...(0)
<223> OTHER INFORMATION: HCV TYPE 1 NS4 REGION 2

<400> SEQUENCE: 39

gag tgc gcc tca cac ctc cct tac atc gag cag gga gcc cag ctc gcc       48
Glu Cys Ala Ser His Leu Pro Tyr Ile Glu Gln Gly Ala Gln Leu Ala
 1               5                  10                  15

gag caa ttc                                                           57
Glu Gln Phe


<210> SEQ ID NO 40
<211> LENGTH: 19
<212> TYPE: PRT
<213> ORGANISM: Hepatitis C Virus

<400> SEQUENCE: 40

Glu Cys Ala Ser His Leu Pro Tyr Ile Glu Gln Gly Ala Gln Leu Ala
 1               5                  10                  15

Glu Gln Phe


<210> SEQ ID NO 41
<211> LENGTH: 57
<212> TYPE: DNA
<213> ORGANISM: Hepatitis C Virus
<220> FEATURE:
<221> NAME/KEY: CDS
<222> LOCATION: (1)...(57)
<220> FEATURE:
<221> NAME/KEY: misc_feature
<222> LOCATION: (0)...(0)
<223> OTHER INFORMATION: HCV TYPE 2 NS4 REGION 2

<400> SEQUENCE: 41

gaa tgt gcc tct aga gcg gcc ctc att gaa gag ggg cag cgg ata gcc       48
Glu Cys Ala Ser Arg Ala Ala Leu Ile Glu Glu Gly Gln Arg Ile Ala
 1               5                  10                  15

gag atg ctg                                                           57
Glu Met Leu


<210> SEQ ID NO 42
<211> LENGTH: 19
<212> TYPE: PRT
<213> ORGANISM: Hepatitis C Virus

<400> SEQUENCE: 42

Glu Cys Ala Ser Arg Ala Ala Leu Ile Glu Glu Gly Gln Arg Ile Ala
 1               5                  10                  15

Glu Met Leu


<210> SEQ ID NO 43
<211> LENGTH: 57
<212> TYPE: DNA
<213> ORGANISM: Hepatitis C Virus
<220> FEATURE:
```

-continued

```
<221> NAME/KEY: CDS
<222> LOCATION: (1)...(57)
<220> FEATURE:
<221> NAME/KEY: misc_feature
<222> LOCATION: (0)...(0)
<223> OTHER INFORMATION: HCV TYPE 3 NS4 REGION 2

<400> SEQUENCE: 43

gag tgc tcg caa gct gcc cca tat atc gaa caa gct cag gtg ata gcc       48
Glu Cys Ser Gln Ala Ala Pro Tyr Ile Glu Gln Ala Gln Val Ile Ala
 1               5                  10                  15

cac cag ttc                                                            57
His Gln Phe


<210> SEQ ID NO 44
<211> LENGTH: 19
<212> TYPE: PRT
<213> ORGANISM: Hepatitis C Virus

<400> SEQUENCE: 44

Glu Cys Ser Gln Ala Ala Pro Tyr Ile Glu Gln Ala Gln Val Ile Ala
 1               5                  10                  15

His Gln Phe


<210> SEQ ID NO 45
<211> LENGTH: 57
<212> TYPE: DNA
<213> ORGANISM: Hepatitis C Virus
<220> FEATURE:
<221> NAME/KEY: CDS
<222> LOCATION: (1)...(57)
<220> FEATURE:
<221> NAME/KEY: misc_feature
<222> LOCATION: (0)...(0)
<223> OTHER INFORMATION: HCV TYPE 4 NS4 REGION 2

<400> SEQUENCE: 45

gag tgt tcc aaa cac ctt cca cta gtc gag cac ggg ttg caa ctt gct       48
Glu Cys Ser Lys His Leu Pro Leu Val Glu His Gly Leu Gln Leu Ala
 1               5                  10                  15

gag caa ttc                                                            57
Glu Gln Phe


<210> SEQ ID NO 46
<211> LENGTH: 19
<212> TYPE: PRT
<213> ORGANISM: Hepatitis C Virus

<400> SEQUENCE: 46

Glu Cys Ser Lys His Leu Pro Leu Val Glu His Gly Leu Gln Leu Ala
 1               5                  10                  15

Glu Gln Phe


<210> SEQ ID NO 47
<211> LENGTH: 57
<212> TYPE: DNA
<213> ORGANISM: Hepatitis C Virus
<220> FEATURE:
<221> NAME/KEY: CDS
<222> LOCATION: (1)...(57)
<220> FEATURE:
<221> NAME/KEY: misc_feature
<222> LOCATION: (0)...(0)
<223> OTHER INFORMATION: HCV TYPE 5 NS4 REGION 2

<400> SEQUENCE: 47
```

-continued

```
gag tgc tcg acc tcg ctc ccc tat atg gac gag gca cgt gct att gcc       48
Glu Cys Ser Thr Ser Leu Pro Tyr Met Asp Glu Ala Arg Ala Ile Ala
 1               5                   10                  15

ggg caa ttc                                                           57
Gly Gln Phe


<210> SEQ ID NO 48
<211> LENGTH: 19
<212> TYPE: PRT
<213> ORGANISM: Hepatitis C Virus

<400> SEQUENCE: 48

Glu Cys Ser Thr Ser Leu Pro Tyr Met Asp Glu Ala Arg Ala Ile Ala
 1               5                  10                  15

Gly Gln Phe


<210> SEQ ID NO 49
<211> LENGTH: 57
<212> TYPE: DNA
<213> ORGANISM: Hepatitis C Virus
<220> FEATURE:
<221> NAME/KEY: CDS
<222> LOCATION: (1)...(57)
<220> FEATURE:
<221> NAME/KEY: misc_feature
<222> LOCATION: (0)...(0)
<223> OTHER INFORMATION: HCV TYPE 6 NS4 REGION 2

<400> SEQUENCE: 49

gag tgc tct agg cac atc ccc tac ctc gct gag ggc cag cag atc gcc       48
Glu Cys Ser Arg His Ile Pro Tyr Leu Ala Glu Gly Gln Gln Ile Ala
 1               5                   10                  15

gaa cag ttc                                                           57
Glu Gln Phe


<210> SEQ ID NO 50
<211> LENGTH: 19
<212> TYPE: PRT
<213> ORGANISM: Hepatitis C Virus

<400> SEQUENCE: 50

Glu Cys Ser Arg His Ile Pro Tyr Leu Ala Glu Gly Gln Gln Ile Ala
 1               5                  10                  15

Glu Gln Phe


<210> SEQ ID NO 51
<211> LENGTH: 24
<212> TYPE: DNA
<213> ORGANISM: Artificial Sequence
<220> FEATURE:
<223> OTHER INFORMATION: Sense Primer 122

<400> SEQUENCE: 51

ctcaaccgtc actgagagag acat                                            24


<210> SEQ ID NO 52
<211> LENGTH: 24
<212> TYPE: DNA
<213> ORGANISM: Artificial Sequence
<220> FEATURE:
<223> OTHER INFORMATION: Antisense Primer 123

<400> SEQUENCE: 52

gctctcaggt tccgctcgtc ctcc                                            24
```

-continued

<210> SEQ ID NO 53
<211> LENGTH: 18
<212> TYPE: PRT
<213> ORGANISM: Hepatitis C Virus
<220> FEATURE:
<221> NAME/KEY: VARIANT
<222> LOCATION: (0)...(0)
<223> OTHER INFORMATION: HCV TYPE 1 NS4 REGION

<400> SEQUENCE: 53

Arg Pro Ala Val Ile Pro Asp Arg Glu Val Leu Tyr Gln Glu Phe Asp
1 5 10 15

Glu Met

<210> SEQ ID NO 54
<211> LENGTH: 18
<212> TYPE: PRT
<213> ORGANISM: Hepatitis C Virus
<220> FEATURE:
<221> NAME/KEY: VARIANT
<222> LOCATION: (0)...(0)
<223> OTHER INFORMATION: HCV TYPE 1 NS4 REGION

<400> SEQUENCE: 54

Arg Pro Ala Val Val Pro Asp Arg Glu Val Leu Tyr Gln Glu Phe Asp
1 5 10 15

Glu Met

<210> SEQ ID NO 55
<211> LENGTH: 19
<212> TYPE: PRT
<213> ORGANISM: Hepatitis C Virus
<220> FEATURE:
<221> NAME/KEY: VARIANT
<222> LOCATION: (0)...(0)
<223> OTHER INFORMATION: HCV TYPE 1 NS4 REGION

<400> SEQUENCE: 55

Glu Cys Ser Gln His Leu Pro Tyr Ile Glu Gln Gly Met Met Leu Ala
1 5 10 15

Glu Gln Phe

<210> SEQ ID NO 56
<211> LENGTH: 19
<212> TYPE: PRT
<213> ORGANISM: Hepatitis C Virus
<220> FEATURE:
<221> NAME/KEY: VARIANT
<222> LOCATION: (0)...(0)
<223> OTHER INFORMATION: HCV TYPE 1 NS4 REGION

<400> SEQUENCE: 56

Glu Cys Ser Gln His Leu Pro Tyr Ile Glu Gln Gly Met Ala Leu Ala
1 5 10 15

Glu Gln Phe

<210> SEQ ID NO 57
<211> LENGTH: 18
<212> TYPE: PRT
<213> ORGANISM: Hepatitis C Virus
<220> FEATURE:
<221> NAME/KEY: VARIANT
<222> LOCATION: (0)...(0)
<223> OTHER INFORMATION: HCV TYPE 2 NS4 REGION

<400> SEQUENCE: 57

-continued

```
Arg Val Val Val Thr Pro Asp Lys Glu Ile Leu Tyr Glu Ala Phe Asp
 1               5                  10                  15

Glu Met


<210> SEQ ID NO 58
<211> LENGTH: 19
<212> TYPE: PRT
<213> ORGANISM: Hepatitis C Virus
<220> FEATURE:
<221> NAME/KEY: VARIANT
<222> LOCATION: (0)...(0)
<223> OTHER INFORMATION: HCV TYPE 2 NS4 REGION

<400> SEQUENCE: 58

Glu Cys Ala Ser Lys Ala Ala Leu Ile Glu Glu Gly Gln Arg Met Ala
 1               5                  10                  15

Glu Met Leu
```

HEPATITIS-C VIRUS TYPE 4, 5 AND 6

CROSS-REFERENCE TO RELATED APPLICATIONS

This application is a divisional of U.S. patent application Ser. No. 11/676,842, filed Feb. 20, 2007, which is a continuation of U.S. patent application Ser. No. 11/090,952, filed Mar. 25, 2005, which is a divisional of U.S. patent application Ser. No. 08/537,802, filed Dec. 21, 1995, which is the National Stage of International Application No. PCT/GB94/00957, filed May 5, 1994, and published in English as WO 94/25602 on Nov. 10, 1994; the contents of which are herein incorporated by reference in their entirety.

FIELD OF THE INVENTION

The present invention relates to newly elucidated sequences of hepatitis C virus type 4 (HCV-4), and type 5 (HCV-5), and to a newly discovered type 6 (HCV-6). In particular, it relates to the etiologic agent of hepatitis C virus type 4, 5 and 6, and to polynucleotides and immunoreactive polypeptides which are useful in immunoassays for the detection of HCV-4, HCV-5 and HCV-6 in biological samples; and also to the use of antigenic HCV-4, HCV-5 and HCV-6 specific polypeptides in vaccines.

BACKGROUND OF THE INVENTION

Acute viral hepatitis is a disease which may result in chronic liver damage. It is clinically diagnosed by a well-defined set of patient symptoms, including jaundice, hepatic tenderness, and an increase in the serum levels of alanine aminotransferase and aspartate aminotransferase. Serologic immunoassays are generally performed to diagnose the specific type of viral causative agent. Historically, patients presenting with symptoms of hepatitis and not otherwise infected by hepatitis A, hepatitis B, Epstein-Barr or cytomegalovirus were clinically diagnosed as having non-A, non-B hepatitis (NANBH) by default.

For many years, the agent of non-A, non-B hepatitis remained elusive. It has now been established that many cases of NANBH are caused by a distinct virus termed hepatitis C virus (HCV). European Patent Application EP-A-0318216 discloses cDNA sequences derived from one strain of HCV, polynucleotide probes and polypeptides for use in immunoassays. Further information on that strain is provided in European Application EP-A-0388232.

The HCV genome encodes a large polyprotein precursor, which contains structural and non-structural regions. The single protein is apparently cleaved into a variety of proteins after production. Most of the structural and non-structural proteins have now been identified from in vitro RNA translation and expression as recombinant proteins. The C and E regions encode for nucleocapsid structural proteins and for envelope structural proteins, respectively. At least five additional regions follow, which encode for non-structural (NS) protein of undefined function. The organization is believed to be as follows (Alberti (1991) *J. Hepatology* 12:279-282):

5' NCR:C:E1:E2:NS1:NS2:NS3:NS4:NS5 3'

Certain immunoreactive proteins have been described as recombinant proteins, for example C22 (in the core region), C33 (in NS3 region), 5-1-1 and C100 (both in the NS4 region), and NS5 (NS5 region). Current diagnosis of hepatitis C is often based on methods which detect antibodies against the product of the C-100 clone. This clone was produced by ligation of overlapping clones to produce a larger viral antigen (C100) corresponding to part of the NS3-NS4 genomic region. C100 was then fused with the human superoxide dismutase (SOD) gene, expressed in use as a large recombinant fusion protein (C100-3) and used on solid phase to develop radio-labeled (RIA) and enzyme-linked immunosorbent assays (ELISA).

Polynucleotides alleged to be useful for screening for HCV are disclosed in European Patent Specification EP-A-0398748. European Patent Specification EP-A-0414475 purports to disclose the propagation of HCV in culture cells and the production of antigens for use in diagnostics. European Patent Specification EP-A-0445423 discloses what is stated to be an improved immunoassay for detecting HCV antibodies.

Blood banks in the United Kingdom carry out routine testing of blood donors for antibodies to components of HCV. A first generation assay involved the detection of HCV antibodies to C100-3 polypeptides. The C100-3 antibody recognizes a composite polyprotein antigen within non-structural regions of the virus and is a consistent marker of HCV infection. However, in acute infections this antibody is unreliable because of the delay (typically 22 weeks) in seroconversion after exposure. Furthermore, the C100-3 antibody test lacks specificity for the hepatitis C virus.

Second generation antibody tests employ recombinant antigens and/or synthetic linear peptides representing structural antigens from the highly conserved core region of the virus as well as non-structural antigens. However, it is found that some second-generation ELISA tests can yield false-positive reactions. The recombinant immunoblot assay (RIBA-2) incorporating four antigens from the HCV genome, purports to provide a method for identifying genuine-anti-HCV reactivity. However, the result can be "indeterminate". The present workers have reported (Chan et al. (1991) *The Lancet* 338:1391) varying reactivity of HCV-positive blood donors to 5-1-1, C100, C33 and C22 antigens, and compared these with the results of the direct detection of HCV RNA present in the blood samples using polymerase chain reaction (PCR) to amplify HCV polynucleotides. However, the work demonstrates that the unambiguous diagnosis of HCV infections is not yet possible.

Recently there have been discovered further types of HCV that differ considerably in sequence and these have been called HCV-2, 3 and 4. Our patent application WO93/10239 (published on 27 May, 1993) describes certain antigenic sequences of HCV-2, 3 and 4. The sequences disclosed for HCV-4 are in the 5' NCR and core regions only. The former does not code for any protein which might be used in an immunoassay for HCV whilst the core region tends to be conserved.

SUMMARY OF INVENTION

The present invention includes the discovery of a previously unknown type 6 variant of HCV, by a comparison of sequences amplified by polymerase chain reaction (PCR) in certain regions of the HCV genome and confirmed by phylogenetic analysis. The invention has identified polynucleotide sequences and polypeptides which are HCV-4, HCV-5 and HCV-6 specific. These may be used to diagnose HCV-4, HCV-5 and HCV-6 infection and should thus be included in any definitive test for HCV infection.

One aspect of the present invention provides a polynucleotide having a nucleotide sequence unique to hepatitis virus type 4, 5 or 6. The sequences are unique to the HCV type concerned in the sense that the sequence is not shared by any other HCV type, and can thus be used to uniquely detect that HCV-type. Sequence variability between HCV 4, 5 and 6 has been found particularly in the NS4, NS5 and core regions and it is therefore from these regions in particular that type-specific polynucleotides and peptides may be obtained. The term type-specific indicates that a sequence unique to that HCV type is involved. Moreover, within each HCV type a number of sub-types may exist having minor sequence variations.

The invention includes NS5 polynucleotide sequences unique to hepatitis C virus types 4 and 6 (HCV-4 and HCV-6); and NS4 sequences unique to HCV-4, HCV-5 and HCV-6 respectively. The sequences may be RNA or DNA sequences, including cDNA sequences. If necessary the DNA sequences may be amplified by polymerase chain reaction. DNA sequences can be used as a hybridization probe. The sequences may be recombinant (i.e. expressed in transformed cells) or synthetic and may be comprised within longer sequences if necessary. Equally, deletions, insertions or substitutions may also be tolerated if the polynucleotide may still function as a specific probe. Polynucleotide sequences which code for antigenic proteins are also particularly useful.

Another aspect of the invention provides a peptide having an amino acid sequence unique to hepatitis virus type 4, 5 or 6.

The invention includes antigenic HCV-4 or HCV-6 specific polypeptide from the NS5 region, or antigenic HCV-4, HCV-5 or HCV-6 specific polypeptide from the NS4 region; or polypeptides including these antigens. A plurality of copies of the peptide may be bound to a multiple antigen peptide core.

The peptide may be labeled to facilitate detection, and may for example be labeled antigenic HCV-4 or HCV-6 specific polypeptide from the NS5 region, or labeled antigenic HCV-4, HCV-5 or HCV-6 specific polypeptide from the NS4 region; (or mixtures thereof) for use in an immunoassay to detect the corresponding antibodies.

It should be understood that the polypeptides will not necessarily comprise the entire NS4 or NS5 region, but that characteristic parts thereof (usually characteristic epitopes) unique to a particular type of HCV may also be employed.

A further aspect of the invention provides antibodies to the peptides, especially to HCV-4 or HCV-6 NS5 antigens, or to HCV-4, HCV-5 or HCV-6 NS4 antigens, particularly monoclonal antibodies for use in therapy and diagnosis. Thus labeled antibodies may be used for in vivo diagnosis. Antibodies carrying cytotoxic agents may be used to attack HCV-4, HCV-5 or HCV-6 infected cells.

A further aspect of the invention provides a vaccine comprising immunogenic peptide, especially HCV-4 or HCV-6 NS5 polypeptide, or immunogenic HCV-4, HCV-5 or HCV-6 NS4 polypeptide.

A further aspect of the invention provides a method of in vitro HCV typing which comprises carrying out endonuclease digestion of an HCV-containing sample to provide restriction fragments, the restriction pattern being characteristic of HCV-4, HCV-5 or HCV-6.

Finally, the present invention also encompasses assay kits including polypeptides which contain at least one epitope of HCV-4, HCV-5 or HCV-6 antigen (or antibodies thereto), as well as necessary preparative reagents, washing reagents, detection reagents and signal producing reagents.

DESCRIPTION OF FIGURES

FIG. 1 is a comparison of inferred amino acid sequences of part of the NS5 region of HCV types 4 (SEQ ID NOS:14 and 16) and 6 (SEQ ID NO:18) (in comparison to type la (SEQ ID NOS:1-9)) from Example 1. The number of sequences compared is shown in the second column. Single amino acid codes are used. The position and frequency of variability within an HCV type is indicated by a subscript.

FIG. 2 gives corresponding DNA nucleotide sequences in the NS5 region of HCV-4 (SEQ ID NOS:10, 13, and 15) and of HCV-6 (SEQ ID NO:17).

FIG. 4 shows DNA primer sequences (SEQ ID NOS:19-22) as used in Example 2 for the PCR amplification of two regions of the NS4 region of HCV-4, HCV-5 and HCV-6.

FIG. 5 shows DNA and amino acid sequences for two partial regions of the NS4 region of HCV-4 (NS4 Region 1: SEQ ID NOS:31 and 32; NS4 Region 2: SEQ ID NOS:45 and 46), HCV-5 (NS4 Region 1: SEQ ID NOS:33 and 34; NS4 Region 2: SEQ ID NOS:47 and 48) and HCV-6 (NS4 Region 1: SEQ ID NOS:35 and 36; NS4 Region 2: SEQ ID NOS:49 and 50) deduced from the nucleotide sequences elucidated in Example 2; for comparison the corresponding regions of HCV-1 (NS4 Region 1: SEQ ID NOS:23, 24, 25 and 26; NS4 Region 2: SEQ ID NOS:37, 38, 39 and 40), HCV-2 (NS4 Region 1: SEQ ID NOS:27 and 28; NS4 Region 2: SEQ ID NOS:41 and 42) and HCV-3 (NS4 Region 1: SEQ ID NOS:29 and 30; NS4 Region 2: SEQ ID NOS:43 and 44) are given, HCV-3 regions 1 and 2 corresponding to amino acids 1691-1708 and 1710-1728 respectively of FIG. 9*b* of W093/10239 (see also Simmonds et al. (1993) *J. Clin. Microb.* 31:1493).

DETAILED DESCRIPTION

Figure 3:
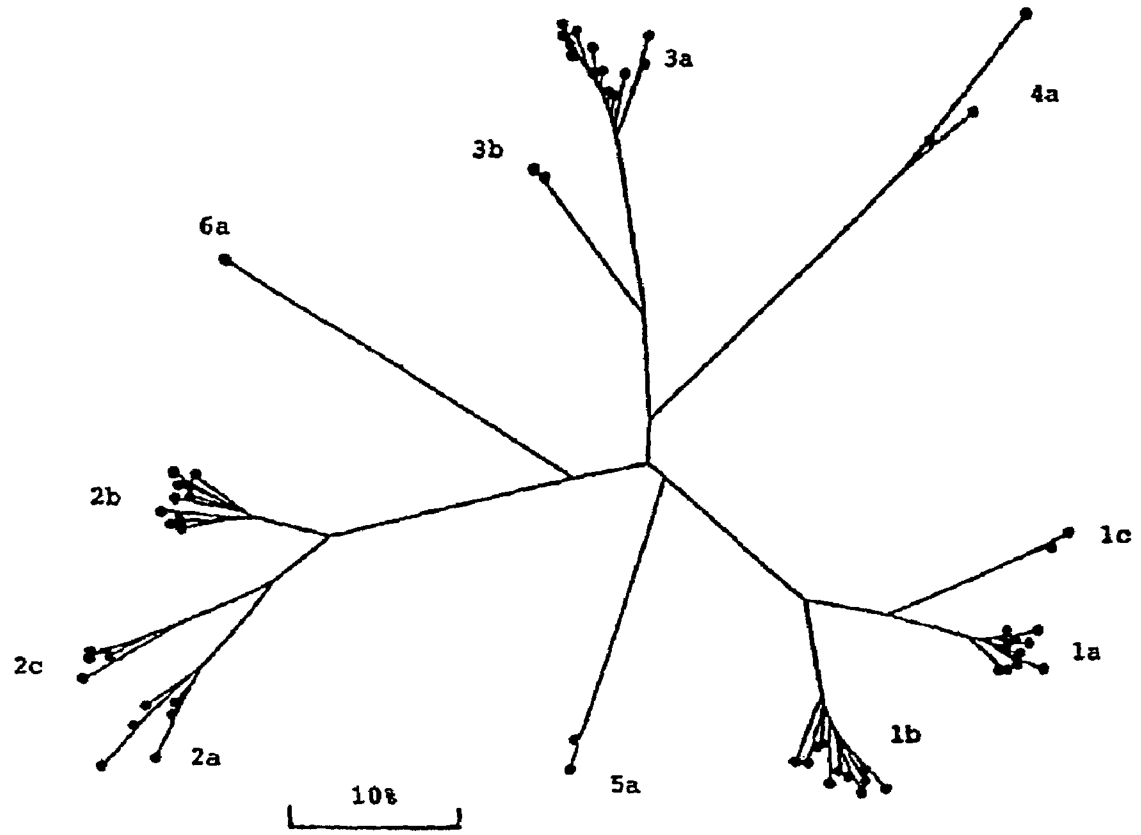
FIG. 3 is a phylogenetic analysis of NS5 sequences from 67 isolates of HCV, showing major HCV types (numbered 1-6) and subtypes (designated a,b,c) and demonstrating that HCV-4 and HCV-6 are distinct types. The sequence distance is proportional to the spacing on the tree according to the indicated scale.

The HCV-4, HCV-5 or HCV-6 specific polynucleotide sequences may be used for identification of the HCV virus itself (usually amplified by PCR) by hybridization techniques.

Oligonucleotides corresponding to variable regions, e.g. in the NS5 or NS4 region, could be used for type-specific PCR. Outer sense and inner sense primers may be used in combination with the two conserved anti-sense primers for a specific detection method for HCV types 4, 5 and 6.

The present invention also provides expression vectors containing the DNA sequences as herein defined, which vectors being capable, in an appropriate host, of expressing the DNA sequence to produce the peptides as defined herein. The expression vector normally contains control elements of DNA that effect expression of the DNA sequence in an appropriate host. These elements may vary according to the host but usually include a promoter, ribosome binding site, translational start and stop sites, and a transcriptional termination site. Examples of such vectors include plasmids and viruses. Expression vectors of the present invention encompass both extrachromosomal vectors and vectors that are integrated into the host cell's chromosome. For use in *E. coli*, the expression vector may contain the DNA sequence of the present invention optionally as a fusion linked to either the 5'- or 3'-end of the DNA sequence encoding, for example, B-galactosidase or the 3'-end of the DNA sequence encoding, for example, the trp E gene.

For use in the insect baculovirus (AcNPV) system, the DNA sequence is optionally fused to the polyhedrin coding sequence.

The present invention also provides a host cell transformed with expression vectors as herein defined. Examples of host cells of use with the present invention include prokaryotic and eukaryotic cells, such as bacterial, yeast, mammalian and insect cells. Particular examples of such cells are *E. coli, S. cerevisiae, P. pastoris*, Chinese hamster ovary and mouse cells, and *Spodoptera frugiperda* and *Tricoplusia ni*. The choice of host cell may depend on a number of factors but, if post-translational modification of the HCV viral peptide is important, then a eukaryotic host would be preferred.

The present invention also provides a process for preparing a peptide as defined herein which comprises isolating the DNA sequence, as herein defined, from the HCV genome, or synthesizing DNA sequence encoding the peptides as defined herein, or generating a DNA sequence encoding the peptide, inserting the DNA sequence into an expression vector such that it is capable, in an appropriate host, of being expressed, transforming host cells with the expression vector, culturing the transformed host cells, and isolating the peptide.

The DNA sequence encoding the peptide may be synthesized using standard procedures (Gait, Oligonucleotide Synthesis: A Practical Approach, 1984, Oxford, IRL Press).

The desired DNA sequence obtained as described above may be inserted into an expression vector using known and standard techniques. The expression vector is normally cut using restriction enzymes and the DNA sequence inserted using blunt-end or staggered-end ligation. The cut is usually made at a restriction site in a convenient position in the expression vector such that, once inserted, the DNA sequences are under the control of the functional elements of DNA that effect its expression.

Transformation of a host cell may be carried out using standard techniques. Some phenotypic marker is usually employed to distinguish between the transformants that have successfully taken up the expression vector and those that have not. Culturing of the transformed host cell and isolation of the peptide as required may also be carried out using standard techniques.

The peptides of the present invention may thus be prepared by recombinant DNA technology, or may be synthesized, for example by using an automatic synthesizer. The term "peptide" (and "polypeptide") is used herein to include epitopic peptides having the minimum number of amino acid residues for antigenicity, through oligopeptides, up to proteins. The peptide may be a recombinant peptide expressed from a transformed cell, or could be a synthetic peptide produced by chemical synthesis.

Antibody specific to a peptide of the present invention can be raised using the peptide. The antibody may be used in quality control testing of batches of the peptides; purification of a peptide or viral lysate; epitope mapping; when labeled, as a conjugate in a competitive type assay, for antibody detection; and in antigen detection assays.

Polyclonal antibody against a peptide of the present invention may be obtained by injecting a peptide, optionally coupled to a carrier to promote an immune response, into a mammalian host, such as a mouse, rat, sheep or rabbit, and recovering the antibody thus produced. The peptide is generally administered in the form of an injectable formulation in which the peptide is admixed with a physiologically acceptable diluent. Adjuvants, such as Freund's complete adjuvant (FCA) or Freund's incomplete adjuvant (FIA), may be included in the formulation. The formulation is normally injected into the host over a suitable period of time, plasma samples being taken at appropriate intervals for assay for anti-HCV viral antibody. When an appropriate level of activity is obtained, the host is bled. Antibody is then extracted and purified from the blood plasma using standard procedures, for example, by protein A or ion-exchange chromatography.

Monoclonal antibody against a peptide of the present invention may be obtained by fusing cells of an immortalizing cell line with cells which produce antibody against the viral of topographically related peptide, and culturing the fused immortalized cell line. Typically, a non-human mammalian host, such as a mouse or rat, is inoculated with the peptide. After sufficient time has elapsed for the host to mount an antibody response, antibody producing cells, such as the splenocytes, are removed. Cells of an immortalizing cell line, such as a mouse or rat myeloma cell line, are fused with the antibody producing cells and the resulting fusions screened to identify a cell line, such as a hybridoma, that secretes the desired monoclonal antibody. The fused cell line may be cultured and the monoclonal antibody purified from the culture media in a similar manner to the purification of polyclonal antibody.

Diagnostic assays based upon the present invention may be used to determine the presence of absence of HCV infection, and the HCV type involved. They may also be used to monitor treatment of such infection, for example in interferon therapy. In an assay for the diagnosis of viral infection, there are basically three distinct approaches that can be adopted involving the detection of viral nucleic acid, viral antigen or viral antibody respectively. Viral nucleic acid is generally regarded as the best indicator of the presence of the virus itself and would identify materials likely to be infectious. However, the detection of nucleic acid is not usually as straightforward as the detection of antigens or antibodies since the level of target can be very low. Viral antigen is used as a marker for the presence of virus and as an indicator of infectivity. Depending upon the virus, the amount of antigen present in a sample can be very low and difficult to detect. Antibody detection is relatively straightforward because, in effect, the host immune system is amplifying the response to an infection by producing large amounts of circulating antibody. The nature of the antibody response can often be clinically useful, for example IgM rather than IgG class antibodies are indicative of a recent infection, or the response to a particular viral antigen may be associated with clearance of the virus. Thus the exact approach adopted for the diagnosis of a viral infection depends upon the particular circumstances and the information sought. In the case of HCV, a diagnostic assay may embody any one of these three approaches.

In any assay for the diagnosis of HCV involving detection of viral nucleic acid, the method may comprise hybridizing viral RNA present in a test sample, or cDNA synthesized from such viral RNA, with a DNA sequence corresponding to the nucleotide sequences of the present invention or encoding a peptide of the invention, and screening the resulting nucleic acid hybrids to identify any HCV viral nucleic acid. The application of this method is usually restricted to a test sample of an appropriate tissue, such as a liver biopsy, in which the viral RNA is likely to be present at a high level. The DNA sequence corresponding to a nucleotide sequence of the present invention or encoding a peptide of the invention may take the form of an oligonucleotide or a cDNA sequence optionally contained within a plasmid. Screening of the nucleic acid hybrids is preferably carried out by using a labeled DNA sequence. Preferably the peptide of the present invention is part of an oligonucleotide wherein the label is situated at a sufficient distance from the peptide so that binding of the peptide to the viral nucleic acid is not interfered with by virtue of the label being too close to the binding site. One or more additional rounds of screening of one kind or another may be carried out to characterize further the hybrids and thus identify any HCV viral nucleic acid. The steps of hybridization and screening are carried out in accordance with procedures known in the art.

A further method for the detection of viral nucleic acid involves amplification of a viral DNA using polymerase chain reaction (PCR). The primers chosen may be specific to the HCV type sequence of interest, so that amplification occurs only with that particular HCV type. Also the size and number of amplified copy sequences may be characteristic of particular HCV types, or they may have characteristic restriction patterns with chosen endonucleases.

In an assay for the diagnosis of HCV involving detection of viral antigen or antibody, the method may comprise contacting a test sample with a peptide of the present invention or a polyclonal or monoclonal antibody against the peptide and determining whether there is any antigen-antibody binding contained within the test sample. For this purpose, a test kit may be provided comprising a peptide, as defined herein, or a polyclonal or monoclonal antibody thereto and means for determining whether there is any binding with antibody or antigen respectively contained in the test sample to produce an immune complex. The test sample may be taken from any of appropriate tissue or physiological fluid, such as blood (serum or plasma), saliva, urine, cerebrospinal fluid, sweat, tears or tissue exudate. If a physiological fluid is obtained, it may optionally be concentrated for any viral antigen or antibody present.

A variety of assay formats may be employed. The peptide can be used to capture selectively antibody against HCV from solution, to label selectively the antibody already captured, or both to capture and label the antibody. In addition, the peptide may be used in a variety of homogeneous assay formats in which the antibody reactive with the peptide is detected in solution with no separation of phases.

The types of assay in which the peptide is used to capture antibody from solution involve immobilization of the peptide on to a solid surface. This surface should be capable of being washed in some way. Examples of suitable surfaces include polymers of various types (molded into microtiter wells; beads; dipsticks of various types; aspiration tips; electrodes; and optical devices); particles (for example latex; stabilized red blood cells; bacterial or fungal cells; spores; gold or other metallic or metal-containing sols; and proteinaceous colloids) with the usual size of the particle being from 0.02 to 5 microns; membranes (for example of nitrocellulose; paper; cellulose acetate; and high porosity/high surface area membranes of an organic or inorganic material).

The attachment of the peptide to the surface can be by passive adsorption from a solution of optimum composition which may include surfactants, solvents, salts and/or chaotropes; or by active chemical bonding. Active bonding may be through a variety of reactive or activatable functional groups which may be exposed on the surface (for example condensing agents; active acid esters, halides and anhydrides; amino, hydroxyl, or carboxyl groups; sulphydryl groups; carbonyl groups; diazo groups; or unsaturated groups). Optionally, the active bonding may be through a protein (itself attached to the surface passively or through active bonding), such as albumin or casein, to which the viral peptide may be chemically bonded by any of a variety of methods. The use of a protein in this way may confer advantages because of isoelectric point, charge, hydrophilicity or other physico-chemical property. The viral peptide may also be attached to the surface (usually but not necessarily a membrane) following electrophoretic separation of a reaction mixture, such as immunoprecipitation.

In the present invention it is preferred to provide blocking peptides which block any cross-reactivity and leave only those HCV antibodies in the sample which will react solely with the type of antigen present in that particular test location. For example, a test location intended to detect HCV-6 will be blocked by a blocking mixture comprising HCV-1 to 5 peptides which will react with all antibodies having reactivity to HCV types 1 to 5 and leave antibodies having only type 6 reactivity.

After contacting the surface bearing the peptide with a test sample (in the presence of a blocking mixture if required), allowing time for reaction, and, where necessary, removing the excess of the sample by any of a variety of means, (such as washing, centrifugation, filtration, magnetism or capillary action) the captured antibody is detected by any means which will give a detectable signal. For example, this may be achieved by use of a labeled molecule or particle as described above which will react with the captured antibody (for example protein A or protein G and the like; anti-species or anti-immunoglobulin-sub-type; rheumatoid factor; or antibody to the peptide, used in a competitive or blocking fashion), or any molecule containing an epitope contained in the peptide. In the present invention, it is preferred to add an anti-human IgG conjugated to horseradish peroxidase and then to detect the bound enzyme by reaction with a substrate to generate a color.

The detectable signal may be produced by any means known in the art such as optical or radioactive or physico-chemical and may be provided directly by labeling the molecule or particle with, for example, a dye, radiolabel, fluorescent, luminescent, chemiluminescent, electroactive species, magnetically resonant species or fluorophore, or indirectly by labeling the molecule or particle with an enzyme itself capable of giving rise to a measurable change of any sort. Alternatively the detectable signal may be obtained using, for example, agglutination, or through a diffraction or birefrigent effect if the surface is in the form of particles.

Assays in which a peptide itself is used to label an already captured antibody require some form of labeling of the peptide which will allow it to be detected. The labeling may be direct by chemically or passively attaching for example a radiolabel, magnetic resonant species, particle of enzyme label to the peptide; or indirect by attaching any form of label to a molecule which will itself react with the peptide. The chemistry of bonding a label to the peptide can be directly through a moiety already present in the peptide, such as an amino group, or through an intermediate moiety, such as a maleimide group. Capture of the antibody may be on any of the surfaces already mentioned in any reagent including passive or activated adsorption which will result in specific antibody or immune complexes being bound. In particular, capture of the antibody could be by anti-species or anti-immunoglobulin-sub-type, by rheumatoid factor, proteins A, G and the like, or by any molecule containing an epitope contained in the peptide.

The labeled peptide may be used in a competitive binding fashion in which its binding to any specific molecule on any of the surfaces exemplified above is blocked by antigen in the sample. Alternatively, it may be used in a non-competitive fashion in which antigen in the sample is bound specifically or non-specifically to any of the surfaces above and is also bound to a specific bi- or poly-valent molecule (e.g. an antibody) with the remaining valencies being used to capture the labeled peptide.

Often in homogeneous assays the peptide and an antibody are separately labeled so that, when the antibody reacts with the recombinant peptide in free solution, the two labels interact to allow, for example, non-radiative transfer of energy captured by one label to the other label with appropriate detection of the excited second label or quenched first label (e.g. by fluorimetry, magnetic resonance or enzyme measurement). Addition of either viral peptide or antibody in a sample results in restriction of the interaction of the labeled pair and thus in a different level of signal in the detector.

A further possible assay format for detecting HCV antibody is the direct sandwich enzyme immunoassay (EIA) format. An antigenic peptide is coated onto microtiter wells. A test sample and a peptide to which an enzyme is coupled are added simultaneously. Any HCV antibody present in the test sample binds both to the peptide coating the well and to the enzyme-coupled peptide. Typically, the same peptide are used on both sides of the sandwich. After washing, bound enzyme is detected using a specific substrate involving a color change.

It is also possible to use IgG/IgM antibody capture ELISA wherein an antihuman IgG and/or IgM antibody is coated onto a solid substrate. When a test sample is added, IgG and/or IgM present in the sample will then bind to the antihuman antibody. The bound IgG and/or IgM represents the total population of those antibodies. A peptide of the present invention will bind only to those IgG and/or IgM antibodies that were produced in response to the antigenic determinant(s) present in the peptide i.e. to those antibodies produced as a result of infection with the type of HCV from which the peptide was derived. For detection of the peptide/antibody complex the peptide may itself have been labeled directly or, after interaction with the captures antibodies, the peptide mad be reacted with a labeled molecule that binds to the peptide.

It can thus be seen that the peptides of the present invention may be used for the detection of HCV infection in many formats, namely as free peptides, in assays including classic ELISA, competition ELISA, membrane bound EIA and immunoprecipitation. Peptide conjugates may be used in amplified assays and IgG/IgM antibody capture ELISA.

An assay of the present invention may be used, for example, for screening donated blood or for clinical purposes, for example, in the detection, typing and monitoring of HCV infections. For screening purposes, the preferred assay formats are those that can be automated, in particular, the microtiter plate format and the bead format. For clinical purposes, in addition to such formats, those suitable for smaller-scale or for single use, for example, latex assays, may also be used. For confirmatory assays in screening procedures, antigens may be presented on a strip suitable for use in Western or other immunoblotting tests.

As indicated above, assays used currently to detect the presence of anti-HCV antibodies in test samples, particularly in screening donated blood, utilize antigenic peptides obtained from HIV type 1 only and such antigens do not reliable detect other HCV genotypes. Accordingly, it is clearly desirable to supplement testing for HIV-1 with testing for all other genotypes, for example, types 2, 3, 4, 5 and 6 and also any further genotypes that may be discovered.

In particular, the invention allows blood donor screening by conventional assays (using HCV type 1 encoded antigens) to be supplemented with a second test that contains oligopeptides corresponding to antigenic regions found for example in the NS5 sequence of HCV-4 or HCV-6, or the NS4 sequence of HCV-4, HCV-5 or HCV-6.

To test for a spectrum of genotypes, there may be provided a series of assay means each comprising one or more antigenic peptides from one genotype of HCV, for example, a series of wells in a microtiter plate, or an equivalent series using the bead format. Such an assay format may be used to determine the type of HCV present in a sample. Alternatively, or in addition, an assay means may comprise antigenic peptides from more than one type, for example, a microwell or bead may be coated with peptides from more than one type.

Oligopeptides corresponding to the antigenic regions of HCV-4, HCV-5 or HCV-6 may also be used separately to distinguish individuals infected with these different HCV types. Such an assay could be in the format of an indirect enzyme immunoassay (EIA) that used sets of wells or beads coated with oligopeptides of the antigenic regions for HCV types 4, 5 and 6. Minor degrees of cross-reactivity, should they exist, can be absorbed out by dilution of the test serum in a diluent that contained blocking amounts of soluble heterologous-type oligopeptides, to ensure that only antibody with type-specific antibody reactivity bound to the solid phase.

It may be advantageous to use more than one HCV antigen for testing, in particular, a combination comprising at least one antigenic peptide derived from the structural region of the genome and at least one antigenic peptide derived from the non-structural region, especially a combination of a core antigen and at least one antigen selected from the NS3, NS4 and NS5 regions. The wells or beads may be coated with the antigens individually. It may be advantageous, however, to fuse two or more antigenic peptides as a single polypeptide, preferably as a recombinant fusion polypeptide. Advantages of such an approach are that the individual antigens can be combined in a fixed, predetermined ratio (usually equimolar) and that only a single polypeptide needs to be produced, purified and characterized. One or more such fusion polypeptides may be used in an assay, if desired in addition to one or more unfused peptides. It will be appreciated that there are many possible combinations of antigens in a fusion polypeptide, for example, a fusion polypeptide may comprise a desired range of antigens from one type only, or may comprise antigens from more than one type.

To obtain a polypeptide comprising multiple peptide antigens by an expression technique, one approach is to fuse the individual coding sequences into a single open reading frame. The fusion should, of course, be carried out in such a manner that the antigenic activity of each component peptide is not significantly compromised by its position relative to another peptide. Particular regard should of course be had for the nature of the sequences at the actual junction between the peptides. The resulting coding sequence can be expressed, for example, as described above in relation to recombinant peptides in general. The methods by which such a fusion polypeptide can be obtained are known in the art, and the production of a recombinant fusion polypeptide comprising multiple antigens of a strain of HCV type 1 is described in GB-A-2 239 245. Peptide conjugates may be used in amplified assays and IgG/IgM antibody capture ELISA.

The peptide of the present invention may be incorporated into a vaccine formulation for inducing immunity to HCV in man. The vaccine may include antigens of HCV types 1 to 6. For this purpose the peptide may be presented in association with a pharmaceutically acceptable carrier. For use in a vaccine formulation, the peptide may optionally be presented as part of a hepatitis B core fusion particle, as described in Clarke et al. (1987) *Nature* 330:381-384, or a polylysine based polymer, as described in Tam (1988) *Proc. Natl. Acad. Sci. U.S.A.* 85:5409-5413. Alternatively, the peptide may optionally be attached to a particulate structure, such as lipsomes or ISCOMS.

Pharmaceutically, acceptable carriers for the vaccine include liquid media suitable for use as vehicles to introduce the peptide into a patient. An example of such liquid media is saline solution. The peptide may be dissolved or suspended as a solid in the carrier. The vaccine formulation may also contain an adjuvant for stimulating the immune response and thereby enhancing the effect of the vaccine. Examples of adjuvants include aluminum hydroxide and aluminum phosphate. The vaccine formulation may contain a final concentration of peptide in the range from 0.01 to 5 mg/ml, preferably from 0.03 to 2 mg/ml. The vaccine formulation may be incorporated into a sterile container, which is then sealed and stored at a low temperature, for example 4 degree C., or may be freeze-dried.

In order to induce immunity in man to HCV, one or more doses of the vaccine formulation may be administered. Each dose may be 0.1 to 2 ml, preferably 0.2 to 1 ml. A method for inducing immunity to HCV in man, comprises the administration of an effective amount of a vaccine formulation, as hereinbefore defined. The present invention also provides the use of a peptide as herein defined in the preparation of a vaccine for use in the induction of immunity to HCV in man. Vaccines of the present invention may be administered by any convenient method for the administration of vaccines including oral and parenteral (e.g. intravenous, subcutaneous or intramuscular) injection. The treatment may consist of a single dose of vaccine or a plurality of doses over a period of time.

Examples of the invention will now be described by way of example only.

EXAMPLE 1

HCV-4 and HCV-6; NS5 Region Sequences

Samples. Plasma from a total of 16 HCV-infected blood donors in Scotland, Egypt and Hong Kong and from a patient with chronic hepatitis in Lebabon were used for analysis of NS5 sequences of types 4 and 6.

Nucleotide sequence analysis. To obtain sequences in the NS5 region, viral RNA was reverse transcribed and amplified by polymerase chain reaction (PCR) in a single reaction with previously published primers thought to be highly conserved amongst different variants of HCV (Enomoto et al. (1990) *Biochemical and Biophysical Research Communications* 170:1021-1025). For some sequences, a second PCR was carried out with primers 554 and 555 (Chan et al. (1992) *J. Gen. Virol.* 73:1131-1141) in combination with two new primers, 122 (sense orientation; 5' CTC AAC CGT CAC TGA GAG AGA CAT 3') (SEQ ID NO:51) and 123 (anti-sense; 5' GCT CTC AGG TTC CGC TCG TCC TCC 3') (SEQ ID NO:52). Product DNA was phosphorylated, purified and cloned into the SmaI site of pUC19 (Yanisch-Perron et al. (1985) *Gene* 33:103-107). following the procedures described in Simmonds & Chan (1993) Analysis of viral sequence variation by PCR. In Molecular Virology: A Practical Approach, pp. 109-138. Edited by A. J. Davidson and R. M. Elliot. Oxford IRL Press. Alternatively, amplified DNA was purified and directly sequenced as described in Simmonds et al. (1990) *J. Virol.* 64:5840-5850 and Cha et al. (1992) *Proc. Natl. Acad. Sci. U.S.A.* 89:7144-7148. These methods allowed comparison of a 222 bp fragment of DNA homologous to positions 7975 to 8196 in the prototype virus (numbered as in Choo et al. (1991) *Proc. Natl. Acad. Sci. U.S.A.* 88:2451-2455). The results are shown in FIGS. 1 and 2.

EXAMPLE 2

HCV-4, -5 and -6; NS4 Region Sequences

Attempts have been made to isolate DNA sequences from the NS4 region of Hepatitis C virus (HCV) types 4, 5 and 6 using PCR amplification. The decision was made to use primers which contained restriction sites, thereby allowing the cloning of the PCR products via cohesive end cloning. New primers were also designed from relatively conserved regions of the HCV NS4 gene. The cloning strategy involved several particular steps, as follows.

(i) Klenow repair. The termini of the amplified DNA were repaired with Klenow DNA polymerase to ensure that the ends which contained the restriction sites were complete.

(ii) Kinasing of termini. The PCR product termini were phosphorylated using T4 polynucleotide kinase. This allowed self-ligation of the products in a concatemerization step.

(iii) Concatemerization of the PCR products. The DNA fragments were ligated together to form long concatemeric arrays. This step internalized the restriction sites encoded in the ends of the primers which greatly increased the efficiency of the cleavage step.

(iv) Restriction digestion. The PCR products were digested overnight with the required restriction enzyme to expose the cohesive ends.

(v) Ligation to the plasmid vector.

General procedures and reagents are described in Maniatis et al. "Molecular Cloning: A Laboratory Manual," Cold Spring Harbor Laboratory, Cold Spring Harbor: N.Y.

PCR Amplification of NS4 Sequences

After cDNA synthesis using primer 007, three rounds of PCR amplification were carried out. Types 4 and 5 were amplified by one round using 007, and 435, followed by two rounds using 5351 and 5943 (which both encode BamHI restriction sites). Type 6 sequences were amplified by one round using 007 plus 253, 281 and 221, followed by two rounds using 5351 and 5943. The products of a minimum of 5 third round reactions were pooled for the cloning steps. The efficiency of the final ligation into the vector appeared to be dependant on a high concentration of the amplified DNA. The primer sequences are listed in FIG. 4.

Cloning

The PCR products were isolated by excision from a conventional agarose gel (0.5× tris acetate EDTA (TAE)). The DNA was reclaimed from the agarose by centrifugation through glass wool. The eluates were pooled in order to increase the total amount of DNA. The DNA was retrieved from the TAE eluate by ethanol precipitation. (The pelleted DNA contained some chemically inert debris from the agarose but this did not interfere with the following steps prior to ligation into the vector. Magic prep columns (Promega) could be used, but ethanol precipitation is simpler, cheaper and more efficient if dealing with a large volume of TAE eluate).

Klenow Repair

The precipitated DNA pellets were resuspended in a 50 ul Klenow reaction mixture comprising:

5 ul polynucleotide kinase buffer (10×),
0.5 ul 3.3 mM dNTPs (final concentration 33 uM),
at least 100 ng of purified PCR fragment,
distilled water to 50 ul, and
5 units Klenow DNA polymerase (10× means that the reagent was added at 10 times the desired final concentration in the reaction mixture)

Incubation was carried out for 30 min at 37 degree C., followed by heat inactivation for 10 min at 75 degree C. The Klenow reaction repairs the ends where the BamHI restriction sites are located. T4 DNA polymerase should not be used for this reaction as it will remove the sites by its exonuclease activity.

Kinasing of Ends

To the above reaction mixture, the following were added:

5 ul 100 mM rATP, and 10 units T4 polynucleotide kinase

This reaction mixture was incubated at 37 degree C. for 30-60 min and heat inactivated as before.

Concatemerization

The PCR products were then concatemerized to internalize the BamHI restriction sites within large multimers. To the phosphorylation reaction, the following were added:

6 ul 10× ligase buffer, and 5 units of T4 DNA ligase

The ligation was incubated overnight at 15 degree C. The concatemerization reaction was heat inactivated as described previously.

Restriction Digestion

The concatemerized PCR products were digested into monomers using BamHI restriction enzyme which simultaneously exposed the cohesive termini. The following were added to the heat inactivated ligation reaction mixture:

6 ul 10× B buffer (Boehringer), and 10-20 units BamHI

The digestion mixture was incubated overnight at 37 degree C. Although the enzyme is not totally inactivated by heat, the reaction mixture was heat treated as before anyway. At this point, the DNA was purified by a Magic prep column to remove cleaved ends. The DNA was eluted from the Magic prep column in 10 ul in order to be as concentrated as possible.

Ligation to Vector 100 ng of bacterial plasmid vector pUC18 was used in the ligation. The plasmid vector DNA had been BamHI-cleaved and purified using "Geneclean" (Bio 101), but not dephosphorylated. (We found that the dephosphorylation reaction lowered the ligation efficiency of the vector to a great extent.) It was planned that blue-white color selection as described hereafter would be sufficient to identify clones. The ligation reaction mixture contained the following:

110 ul of purified insert DNA produced as above 5 ul plasmid vector DNA, 1.5 ul 10× ligase buffer, and 1 unit of ligase The reaction mixture was incubated overnight at 15 degree C.

Transformation of *E. coli*

Bacterial transformations were carried out using the cell strain, XL-1 Blue (Stratagene). Cells were made competent for transformation by standard calcium chloride methods and stored quick-frozen in a glycerol/calcium chloride suspension in 200 ul aliquots. 3 ul of the ligation reaction product were used to transform 100 ul of rapidly thawed competent XL-1 Blue cells (10 min on ice, 2 min at 42 degree C., 1 hour at 37 degree C. with shaking after addition of 1 ml of L broth). The cells were plated in 200 ul aliquots onto L agar plates containing X-Gal (20 ug/ml), IPTG (0.1 mM), Ap (50 ug/ml) and Tet (12.5 ug/ml). The presence of the chemicals IPTG (isopropyl-.beta.-D-thiogalactopyranoside) and X-gal (5-bromo-4-chloro-3-indolyl-.beta.-D-galactopyranoside) in the media produces a blue color in colonies which contain plasmids such as the pUC series which encode the lacZ enzymic peptide. The insertion of cloned DNA into the polylinker region of these plasmids interrupts the lacZ peptide sequence, thereby destroying the ability of the plasmid to produce the enzyme. Bacterial colonies which contain recombinant plasmids will, therefore, be white.

Analysis of White Colonies

Blue-white selection identified cell colonies which contained recombinant plasmids. These colonies were picked and DNA was prepared from them by mini-plasmid preparations. Digestion of the DNA with BamHI confirmed that the plasmids contained cloned inserts. The plasmid DNA was purified by glassmilk and sequenced using the USB Sequenase kit with M13 forward and reverse primers.

Discussion

Although this protocol contains a large number of steps, it is simple to execute. Further work has found that the method has a high degree of reproducibility. Theoretically, this cloning strategy should not work if the PCR product contains an internal BamHI site. However, the NS4 sequence which was obtained for type 6 did contain such an internal site; and there are no obvious reasons why foreshortened type 6 sequences were not in fact the predominant product of the cloning experiment.

FIG. 5 shows the DNA and amino acid sequences for two regions or NS4 in respect at HCV types 1 to 6 (for comparison) and types 4 to 6.

EXAMPLE 3

Synthesis of NS4 Peptides

The following peptides within the NS4 region of HCV types 1 to 6 were synthesized. Types 4 to 6 are novel sequences according to the present invention, whereas types 1 to 3 are presented for comparison purposes and use in a complete HCV serotyping assay.

HCV type 1 (SEQ ID NO:26)
$[H_2N$-KPAIIPDREVLYREFDEM$]_8K_4K_2K$-COOH (MDL031)

HCV type 1 (SEQ ID NO:24)
$[H_2N$-KPAVIPDREVLYREFDEM$]_8K_4K_2K$-COOH (MDL033)

HCV type 1 (SEQ ID NO:53)
$[H_2N$-RPAVIPDREVLYQEFDEM$]_8K_4K_2K$-COOH (MDL036)

HCV type 1 (SEQ ID NO:54)
$[H_2N$-RPAVVPDREVLYQEFDEM$]_8K_4K_2K$-COOH (MDL035)

HCV type 1 (SEQ ID NO:55)
$[H_2N$-ECSQHLPYIEQGMMLAEQF$]_8K_4K_2K$-COOH (MDL037Q)

HCV type 1 (SEQ ID NO:56)
$[H_2N$-ECSQHLPYIEQGMALAEQF$]_8K_4K_2K$-COOH (MDL038Q)

HCV type 2 (SEQ ID NO:57)
$[H_2N$-RVVVTPDKEILYEAFDEM$]_8K_4K_2K$-COOH (MDL039)

HCV type 2 (SEQ ID NO:42)
$[H_2N$-ECASRAALIEEGQRIAEML$]_8K_4K_2K$-COOH (MDL041)

HCV type 2 (SEQ ID NO:58)
$[H_2N$-ECASKAALIEEGQRMAEML$]_8K_4K_2K$-COOH (MDL040)

-continued

HCV type 3
(SEQ ID NO:30)
$[H_2N$-KPALVPDKEVLYQQYDEM$]_8K_4K_2K$-COOH (MDL042)

HCV type 3
(SEQ ID NO:44)
$[H_2N$-ECSQAAPYIEQAQVIAHQF$]_8K_4K_2K$-COOH (MDL044)

HCV type 4
(SEQ ID NO:32)
$[H_2N$-QPAVIPDREVLYQQFEDEM$]_8K_4K_2K$-COOH (MDL034)

HCV type 4
(SEQ ID NO:46)
$[H_2N$-ECSKHLPLVEHGLQLAEQF$]_8K_4K_2K$-COOH (MDL028)

HCV type 5
(SEQ ID NO:34)
$[H_2N$-RPAIIPDREVLYQQFDKM$]_8K_4K_2K$-COOH (MDL024)

HCV type 5
(SEQ ID NO:48)
$[H_2N$-ECSTSLPYMDEARAIAGQF$]_8K_4K_2K$-COOH (MDL029)

HCV type 6
(SEQ ID NO:36)
$[H_2N$-KPAVVPDREILYQQFDEM$]_8K_4K_2K$-COOH (MDL025)

HCV type 6
(SEQ ID NO:50)
$[H_2N$-ECSRHIPYLAEGQQIAEQF$]_8K_4K_2K$-COOH (MDL022)

Synthesis of Multiple Antigenic Peptide MDL029

In order to work successfully, the serotyping assay requires that peptides are synthesized on a special resin support, bearing the multiple antigen peptide core ($K_4K_2K$) as developed by Tam (Tam (1988) *Proc. Natl. Acad. Sci. USA.* 85:5409:5413). All peptides were synthesized on an Applied Biosystems model 432A Synergy peptide synthesizer running FASTmoC™ chemistry. Peptide synthesis was achieved using the standard run program without modification. All reagents used were supplied by Applied Biosystems Limited (Kelvin Close, Birchwood Science Park, Warrington, UK). The MAP resin was hepta-lysyl ($K_4K_2K$) core on a polyoxyethylene/polystyrene co-polymer with an HMP linker and beta-alanine internal reference amino acid. The N-a-amino group of all amino acids was protected by the 9-fluorenylmethoxycarbonyl (Fmoc) group. Amino acids with reactive side groups were protected as follows:

| Amino Acid | Code | Protecting Group |
|---|---|---|
| glutamine | Q | tert. Butyl ester (OtBu) |
| cysteine | C | trityl (Trt) |
| serine | S | tert. Butyl (tBu) |
| threonine | T | tert. Butyl (tBu) |
| tyrosine | Y | tert. Butyl (tBu) |
| aspartic acid | D | tert. Butyl ester (OtBu) |
| arginine | R | 2,2,5,7,8-Pentamethylchroman-6-sulphonyl (Pmc) |

The progress of the synthesis was monitored by measuring the conductivity of the coupling and deprotection mixtures. There are no abnormalities in the conductivity trace and the synthesis was considered successful.

Following the synthesis, the fully protected peptide resin was transferred to a conical 50 mL capacity polypropylene tube and treated with thioanisole (0.15 mL), ethandithiol (0.15 mL) and trifluoroacetic acid (TFA; 2.7 mL). The mixture was stirred for three hours at room temperature, then filtered through glass wool in a Pasteur pipette, the filtrate dropping into 20 mL tert. butylmethylether (TMBE) contained in a glass screw-capped bottle, whereupon the peptide precipitated. The tube was centrifuged and the liquor aspirated, leaving the peptide pellet in the tube. Peptide was washed with three further 20 mL aliquots of TMBE, using a spatula to dis-aggregate the pellet and centrifugation to recover the peptide. The peptide was finally dried at room temperature in vacuo.

To analyze the purity of the peptide, a small sample was dissolved in purified water and submitted to analysis by reverse phase high-performance liquid chromatography (HPLC). The reverse phase column was 250×4.6 mm containing a $C_4$ matrix. Peptide was eluted with a gradient of 3.5% acetonitrile to 70% acetonitrile over 20 minutes at a flow rate of 1.5 mL $min^{-1}$. The eluant was monitored at 214 nm to detect peptide.

EXAMPLE 4

Assay for the Determination of HCV Serotypes 1-6

We have developed an assay based on selective competition, which is capable of distinguishing the serotype of HCV to which antibodies present in a biological sample have been produced. Typically the sample will be serum or plasma from a human with confirmed hepatitis C infection.

The assay relies on the selectivity of 17 different synthetic peptides covering variable sequences within the NS4 protein of hepatitis C virus types 1, 2, 3, 4, 5 and 6. Whilst there is a degree of cross-reactivity between antisera raised to NS4 of an HCV serotype and the homologous region of other serotypes, this can be blocked without completely removing the true reactivity. In view of this, we have developed an assay format involving coating wells of a microtiter plate with an equal amount of all 17 peptides. Samples are tested in eight duplicate wells which each receive a different mixture of blocking peptides. Only one testing well and the un-completed control well should contain coloration at the end of the assay protocol, thereby identifying the serotype of the infecting hepatitis C virus.

Plates for serotyping assays are prepared by coating approximately equimolar amounts of each of the peptides onto polystyrene microwell plates. Peptides are dissolved in purified water and a mixture is made at the following concentrations:

| 25 ng/ml | 50 ng/ml |
|---|---|
| MDL031 | MDL039 |
| MDL033 | MDL041 |
| MDL036 | MDL040 |
| MDL035 | MDL042 |
| MDL037Q | MDL044 |
| MDL038Q | MDL034 |
| | MDL028 |
| | MDL024 |
| | MDL029 |
| | MDL025 |
| | MDL022 |

Although strictly speaking each microwell need only contain peptide of the type which it is intended to detect, it is more convenient to coat each microwell with all six antigen types. Peptides were allowed to bind to the plates by adding 100 ul of the peptide mixture into each well of the plate and incubating at +4 degree C. overnight. To provide sufficient differentiation between the various serotypes, it is then necessary to add competing heterologous peptides to the sample being tested. Competing solutions are made up in assay sample diluent to give a 100-fold excess of competing peptide, relative to the coating concentration. The different competing solutions are classified according to the serotype for which they are blocking, i.e. Competing Solution 1 contains peptides for types 2-5. Competing solutions are made to have the excess required in 10 ul. The competing solutions are as follows:

| Competing solution | Peptide | Concentration |
|---|---|---|
| 1 | MDL039 | 50 ug/ml each |
| | MDL041 | |
| | MDL040 | |
| | MDL042 | |
| | MDL044 | |
| | MDL034 | |
| | MDL028 | |
| | MDL024 | |
| | MDL029 | |
| | MDL025 | |
| | MDSL022 | |
| 2 | MDL031 | 25 ug/ml |
| | MDL033 | 25 ug/ml |
| | MDL036 | 25 ug/ml |
| | MDL035 | 25 ug/ml |
| | MDL037Q | 25 ug/ml |
| | MDL038Q | 25 ug/ml |
| | MDL042 | 50 ug/ml |
| | MDL044 | 50 ug/ml |
| | MDL034 | 50 ug/ml |
| | MDL028 | 50 ug/ml |
| | MDL024 | 50 ug/ml |
| | MDL029 | 50 ug/ml |
| | MDL025 | 50 ug/ml |
| | MDL022 | 50 ug/ml |
| 3 | MDL031 | 25 ug/ml |
| | MDL033 | 25 ug/ml |
| | MDL036 | 25 ug/ml |
| | MDL035 | 25 ug/ml |
| | MDL037Q | 25 ug/ml |
| | MDL038Q | 25 ug/ml |
| | MDL039 | 50 ug/ml |
| | MDL040 | 50 ug/ml |
| | MDL041 | 50 ug/ml |
| | MDL034 | 50 ug/ml |
| | MDL028 | 50 ug/ml |
| | MDL024 | 50 ug/ml |
| | MDL029 | 50 ug/ml |
| | MDL025 | 50 ug/ml |
| | MDL022 | 50 ug/ml |
| 4 | MDL031 | 25 ug/ml |
| | MDL033 | 25 ug/ml |
| | MDL036 | 25 ug/ml |
| | MDL035 | 25 ug/ml |
| | MDL037Q | 25 ug/ml |
| | MDL038Q | 25 ug/ml |
| | MDL039 | 50 ug/ml |
| | MDL040 | 50 ug/ml |
| | MDL041 | 50 ug/ml |
| | MDL042 | 50 ug/ml |
| | MDL044 | 50 ug/ml |
| | MDL024 | 50 ug/ml |
| | MDL029 | 50 ug/ml |
| | MDL025 | 50 ug/ml |
| | MDL022 | 50 ug/ml |
| 5 | MDL031 | 25 ug/ml |
| | MDL033 | 25 ug/ml |
| | MDL036 | 25 ug/ml |
| | MDL035 | 25 ug/ml |
| | MDL037Q | 25 ug/ml |
| | MDL038Q | 25 ug/ml |
| | MDL039 | 50 ug/ml |
| | MDL040 | 50 ug/ml |
| | MDL041 | 50 ug/ml |
| | MDL034 | 50 ug/ml |

-continued

| Competing solution | Peptide | Concentration |
|---|---|---|
| | MDL028 | 50 ug/ml |
| | MDL042 | 50 ug/ml |
| | MDL044 | 50 ug/ml |
| | MDL025 | 50 ug/ml |
| | MDL022 | 50 ug/ml |
| 6 | MDL031 | 25 ug/ml |
| | MDL033 | 25 ug/ml |
| | MDL036 | 25 ug/ml |
| | MDL035 | 25 ug/ml |
| | MDL037Q | 25 ug/ml |
| | MDL038Q | 25 ug/ml |
| | MDL039 | 50 ug/ml |
| | MDL040 | 50 ug/ml |
| | MDL041 | 50 ug/ml |
| | MDL034 | 50 ug/ml |
| | MDL028 | 50 ug/ml |
| | MDL024 | 50 ug/ml |
| | MDL029 | 50 ug/ml |
| | MDL042 | 50 ug/ml |
| | MDL044 | 50 ug/ml |

The protocol for using the serotyping assay is as follows:

1) Add 180 ul sample of diluent to each well.
2) Add 10 ul blocking peptides to relevant wells.
3) Add 10 ul sample to each of six wells.
4) Mix plate and incubate at 37 degree C. for 1 hour.
5) Wash wells three times.
6) Add 100 ul conjugate to each well.
7) Incubate at 37 degree C. for 1 hour.
8) Wash wells three times.
9) Add 100 ul TMB solution (including 3,31,5,5'-tetramethylbenzidine, hydrogen peroxide, buffers etc).
10) Incubate at 37 degree C. for 30 minutes.
11) Stop reaction with sulphuric acid; and
12) Read optical density at 450 nm/690 nm.

Samples known to contain anti-HCV antibodies are tested at a dilution of 1/20 with 100 fold excess of competing peptides, in a total volume of 200 ul as described above. Following incubation, sample is removed and the wells are washed. An anti-human immunoglobulin G conjugated to horseradish peroxidase is added, and binds to any captured anti-HCV antibodies. Bound antibody is then visualised by removing the enzyme conjugate and adding a substrate and chromogen, which, in the presence of enzyme, converts from a colorless to a colored solution. The intensity of the color can be measured and is directly proportional to the amount of enzyme present. Results on certain samples are given in Table 1.

TABLE 1

| SAMPLE | NO BLOCK | ALL BLOCK | TYPE 1 | TYPE 2 | TYPE 3 | TYPE 4 | TYPE 5 | TYPE 6 | RESULT |
|---|---|---|---|---|---|---|---|---|---|
| Control 1 | **0.515** | 0.049 | **0.530** | 0.033 | 0.038 | 0.038 | 0.031 | 0.029 | 1 |
| Control 2 | **1.821** | 0.010 | 0.028 | **1.916** | 0.004 | −0.007 | 0.040 | 0.005 | 2 |
| Control 3 | **2.035** | 0.066 | 0.048 | 0.046 | **1.933** | 0.048 | 0.067 | 0.044 | 3 |
| Egypt 3 | **OVER** | 0.372 | 0.346 | 0.478 | 0.322 | **OVER** | 0.256 | 0.430 | 4 |
| C1016116 | **OVER** | 0.456 | 0.635 | 0.480 | 0.533 | 0.533 | **OVER** | 0.617 | 5 |
| Control 6 | **0.082** | 0.004 | 0.007 | −0.003 | −0.004 | −0.012 | −0.011 | **0.067** | 6 |
| PD372 | **OVER** | 0.076 | **1.497** | 0.081 | 0.072 | 0.040 | 0.057 | 0.075 | 1 |
| PD513 | **OVER** | 0.548 | 0.467 | **OVER** | 0.553 | 0.470 | 0.525 | 0.582 | 2 |
| AD558 | **OVER** | 0.031 | 0.064 | 0.044 | **OVER** | 0.035 | 0.054 | 0.048 | 3 |
| Egypt 37 | **OVER** | 0.034 | 0.064 | 0.039 | 0.045 | **1.473** | 0.047 | 0.037 | 4 |
| C1015921 | **0.173** | 0.010 | 0.017 | 0.008 | 0.011 | 0.005 | **0.182** | 0.012 | 5 |

Positive results are shown in bold text.

EXAMPLE 5

Assay for the Determination of HCV Serotypes 4-6

An alternative to the assay format in Example 4 has been developed. This assay is more limited in scope using only the peptides for types 4, 5 and 6. For some samples, the more comprehensive assay may give erroneous results, due to greater cross-reactivity with type 1 peptides. The protocol for performing the more restricted assay is identical to that given in Example 4.

Plates for the HCV types 4-6 assay are prepared as described in Example 4 with the only difference being the reduced number of peptides used. Peptides are dissolved in purified water and a mixture is made at the following concentration:

| | |
|---|---|
| MDL034<br>MDL028<br>MDL024<br>MDL029<br>MDL025<br>MDL022 | 50 ng/ml |

Peptides are allowed to bind to the plates by adding 100 ul of the peptide mixture into each well of the plate and incubating at +4 degree C. overnight.

To provide sufficient differentiation between the various serotypes, it is then necessary to add competing heterologous peptides with the sample being tested. Competing solutions are made up in assay sample diluent to give a 100-fold excess of competing peptide, relative to the coating concentration.

The different competing solutions are classified according to the serotype for which they are blocking, i.e. Competing Solution 4 contains peptides for types 5 and 6. Competing solutions are made to have the excess required in 10 ul. The competing solutions are as follows:

| Competing Solution | Peptide | Concentration |
|---|---|---|
| 4 | MDL024<br>MDL029<br>MDL025<br>MDL022 | 50 ug/ml each |
| 5 | MDL034<br>MDL028 | 50 ug/ml each |

-continued

| Competing Solution | Peptide | Concentration |
|---|---|---|
| | MDL025<br>MDL022 | |
| 6 | MDL034<br>MDL028<br>MDL024<br>MDL029 | 50 ug/ml each |

Samples known to contain anti-HCV antibodies are tested at a dilution of 1/20 with 100 fold excess of competing peptides, in a total volume of 200 ul, as described in Example 4. Following incubation, sample is removed and the wells are washed. An anti-human immunoglobulin G conjugated to horseradish peroxidase is added, and binds to any captured anti-HCV antibodies. Bound antibody is then visualised by removing the enzyme conjugate and adding a substrate and chromogen, which, in the presence of enzyme, converts from a colorless to a colored solution. The intensity of the color can be measured and is directly proportional to the amount of enzyme present. Results on certain samples are given in Table 2.

TABLE 2

| SAMPLE | NO BLOCK | ALL BLOCK | TYPE 4 | TYPE 5 | TYPE 6 |
|---|---|---|---|---|---|
| EGYPT 1 | **OVER** | 0.109 | **1.669** | 0.184 | 0.048 |
| EGYPT 2 | **0.525** | 0.010 | **0.514** | 0.001 | −0.006 |
| EGYPT 3 | **OVER** | 0.269 | **OVER** | 0.329 | 0.201 |
| EGYPT 4 | **0.266** | −0.001 | **0.292** | 0.006 | −0.002 |
| EGYPT 5 | **1.677** | 0.090 | **1.274** | 0.094 | 0.086 |
| EGYPT 6 | **OVER** | 0.208 | **0.317** | 0.041 | 0.022 |
| EGYPT 7 | **OVER** | 0.113 | **OVER** | 0.143 | 0.204 |
| EGYPT 8 | **OVER** | 0.085 | **0.891** | 0.105 | 0.098 |
| EGYPT 9 | **0.051** | 0.009 | **0.055** | 0.014 | 0.022 |
| EGYPT 10 | **OVER** | 0.021 | **2.023** | 0.043 | 0.073 |
| EGYPT 11 | **0.077** | 0.024 | **0.095** | 0.032 | 0.048 |
| C1016116 | **OVER** | 0.647 | 0.778 | **OVER** | 0.513 |
| C1015921 | **0.196** | 0.014 | 0.009 | **0.222** | 0.009 |
| C1132558 | **0.015** | 0.007 | 0.008 | **0.015** | 0.007 |
| K904836 | **OVER** | 0.073 | 0.101 | **OVER** | 0.071 |
| Control 6 | **0.433** | 0.029 | 0.013 | 0.015 | **0.314** |
| HK T3950 | **0.428** | 0.034 | 0.017 | 0.027 | **0.366** |
| HK T3943 | **OVER** | 0.348 | 0.424 | 0.342 | **1.105** |

Positive results are shown in bold text.
NB - The preponderance of Type 4 results reflects the relative incidence and availability or samples for types 4, 5, & 6.

REFERENCES

BROWN, E. A., ZHANG, H., PING, H.-L. & LEMON, S. M. (1992). Secondary structure of the 5' nontranslated region of hepatitis C virus and pestivirus genomic RNAS. Nucleic Acids Research 20, 5041-5045.

BUKH, J., PURCELL, R. H. & MILLER, R. H. (1992a). Importance of primer selection for the detection of hepatitis C virus RNA with the polymerase chain reaction assay. Proceedings of the National Academy of Sciences, U.S.A. 89, 187-191.

BUKH, J., PURCELL, R. H. & MILLER, R. H. (1992b). Sequence analysis of the 5' noncoding region of hepatitis C virus. Proceedings of the National Academy of Sciences, U.S.A. 89, 4942-4946.

CHA, T. A., BEALL, E., IRVINE, B., KOLBERG, J., CHIEN, D., KUO, G. & URDEA, M. S.(1992). At least five related, but distinct, hepatitis C viral genotypes exist. Proceedings of the National Academy of Sciences, U.S.A.89, 7144-7148.

CHAN, S. W. SIMMONDS, P., MCOMISH, F., YAP, P. L., MITCHELL, R., DOW, B. & FOLLETT, E. (1991). Serological reactivity of blood donors infected with three different types of hepatitis C virus. Lancet 338, 1391.

CHAN, S. W., HOLMES, E. C., MCCOMISH, F., FOLLETT, E., YAP, P. I. & SIMMONDS, P. (1992a). Phylogenetic analysis of a new, highly divergent HCV type (type 3): effect of sequence variability on serological responses to infection. Hepatitis C virus and related viruses, Molecular Virology and pathogenesis. First Abstract D5, 73 (Abstract).

CHAN, S. W., MCCOMISH, F., HOLMES, E. C., DOW, B., PEUTHERER, J. F., FOLLETT, E., YAP, P. I. & SIMMONDS, P. (1992b). Analysis of a new hepatitis C virus type and its phylogenetic relationship to existing variants. Journal of General Virology 73, 1131-1141.

CHOO, Q. L., KUO, G., WEINER, A. J., OVERBY, L. R., BRADLEY, D. W. & HOUGHTON, M. (1989). Isolation of a cDNA derived from a blood-borne non-A, non-B hepatitis genome. Science 244, 359-362.

CHOO, Q. L., RICHMAN, K. H., HAN, J. H., BERGER, K., LEE, C., DONG, C., GALLEGOS, C., COIT, D., MEDINA SELBY, R., BARR, P. J., WEINER, A. J., BRADLEY, D. W., KUO, G. & HOUGHTON, M. (1991). Genetic organization and diversity of the hepatitis C virus. Proceedings of the National Academy of Sciences, U.S.A. 88, 2451-2455.

ENOMOTO, N., TAKADA, A., NAKAO, T. & DATE, T. (1990). There are two major types of hepatitis C virus in Japan. Biochemical and Biophysical Research Communications 170, 1021-1025.

FELSENSTEIN, J. (1991). In PHYLIP manual version 3,4 Berkeley: University Herbarium, University of California.

HAN. J. H., SHYAMALA, V., RICHMAN, K. H., BRAUER, M. J., IRVINE, B., URDEA, M. S., TEKAMP OLSON, P., KUO, G., CHOO, Q. L., & HOUGHTON, M. (1991). Characterization of the terminal regions of hepatitis C viral RNA: identification of conserved sequences in the 5' untranslated region and poly(A) tails at the 3' end. Proceedings of the National Academy of Sciences, U.S.A.88, 1711-1715.

HIGGINS, D. G., BLEASBY, A. J. & FUCHS, R. (1992). Clustal V: improved software for multiple sequence alignments. CABIOS 8, 189-191.

HIJIKATA, M., KATO, N., OOTSUYAMA, Y., NAKAGAWA, M., OHKOSHI, S & SHIMOTOHNO, K. (1991). Hypervariable regions in the putative glycoprotein of hepatitis C virus. Biochemical and Biophysical Research Communications 175, 220-228

HOUGHTON. M., WEINER, A., HAN, J., KUO, G. & CHOO, Q. L. (1991). Molecular biology of the hepatitis C viruses: implications for diagnosis, development and control of viral disease. Hepatology 14, 381-388.

INCHAUSPE, G., ZEBEDEE, S., LEE, D., SUGITANI, M., NASOFF, M. & PRINCE, A. M. (1991). Genomic structure of the human prototype strain H of hepatitis C virus: Comparison with American and Japanese isolates. proceedings of the National Academy of Sciences, U.S.A.88, 10292-10296.

KANAI, K., KAKO, M. & OKAMOTO, H. (1992). HCV Genotypes in Chronic Hepatitis-C and Response to Interferon. Lancet 339, 1543.

KATO, N., HIJIKATA, M., OOTSUYAMA, Y., NAKAGAWA, M., OHKOSHI, S., SUGIMURA, T. & SHIMOTOHNO, K. (1990). Molecular cloning of the human hepatitis C virus genome from Japanese patients with non-A, non-B hepatitis. Proceedings of the National Academy of Sciences, U.S.A. 87, 9524-9528.

KATO, N., OOTSUYAMA, Y., OHKOSHI, S., NAKAZAWA, T., MORI, S., HIJIKATA, M. & SHIMOTOHNO, K. (1991). Distribution of plural HCV types in Japan, Biochemical and Biophysical Research Communications 181, 279-285.

KUO, G., CHOO, Q. I., ALTER, H. J., GITNICK, G. I., REDEKER, A. G., PURCELL, R. H., MIYAMURA, T., DIENSTAG, J. I., ALTER, M. J., STEVENS, C. E., TEGTMEIER, F., BONINO, F., COLUMBO, M., LEE, W. S., KUO, C., BERGER, K. SCHUSTER, J. R., OVERBY, L. R., BRADLEY, D. W. & HOUGHTON, M. (1989). An assay for circulating antibodies to a major etiologic virus of human non-A, non-B hepatitis. Science 244, 362-364.

MCOMISH, F., CHAN, S. W., DOW, B. C., GILLON, J., FRAME, W. D., CRAWFORD, R. J., YAP, P. L., FOLLETT, E. A. C. & SIMMONDS, P. (1992). Detection of three types of hepatitis C virus in blood donors: Investigation of type-specific differences in serological reactivity and rate of alanine aminotransferase abnormalities. Transfusion in press.

MILLER, R. H. & PURCELL, R. H. (1990). Hepatitis C virus shares amino acid sequence similarity with pestiviruses and flaviviruses as well as members of two plant virus supergroups. Proceedings of the National Academy of Sciences, U.S.A. 87, 2057-2061.

MORI, S., KATO, N., YAGYU, A., TANAKA, T., IKEDA, Y., PETCHCLAI, B., CHIEWSLIP, P., KURIMURA, T & SHIMOTOHNO, K. (1992). A new type of hepatitis C virus in patients in Thailand. Biochemical and Biophysical Research Communications 183, 334-342.

OGATA, N., ALTER, H. J., MILLER, R. H. & PURCELL, R. H. (1991). Nucleotide sequence and mutation rate of the H strain of hepatitis C virus. Proceedings of the National Academy of Sciences, U.S.A.88, 3392-3396.

OKAMOTO, H., OKADA, S., SUGIYAMA, Y., YOTSUMOTO, S., TANAKA, T., YOSHIZAWA, H., TSUDA, F., MIYAKAWA, Y & MAYUMI, M. (1990). The 5'-terminal sequence of the hepatitis C virus genome. Japanese Journal of Experimental Medicine 60, 167-177.

OKAMOTO, H., OKADA, S., SUGIYAMA, Y., KURAI, K., IIZUKA, H., MACHIDA, A., MIYAKAWA, Y & MAYUMI, M. (1991). Nucleotide sequence of the genomic RNA of hepatitis C virus isolated from a human carrier: comparison with reported isolates for conserved and divergent regions. Journal of General Virology 72, 2697-2704.

OKAMOTO, H., KURAI, K., OKADA, S., YAMAMOTO, K., LIZUKA, H., TANAKA, T., FUKUDA, S., TSUDA, F & MISHIRO, S. (1992). Full-length sequence of a hepatitis C virus genome having poor homology to reported isolates: comparative study of four distinct genotypes. Virology 188, 331-341.

POZZATO, G., MORETTI, M., FRANZIN, F., CROCE, L. S., TIRIBELLI, C., MASAYU, T., KANEKO, S., UNOURA, M. & KOBAYASHI, K. (1991). Severity of liver disease with different hepatitis C viral clones. Lancet 338,509. SAITOU, N., & NEI, M. (1987). The neighbor-joining method: a new method for reconstructing phylogenetic trees. Molecular Biological Evolution 4, 406-425.

SIMMONDS, P., MCOMISH, F., YAP, P. I. CHAN, S. W., LIN, C. K., DUSHEIKO, G. SAEED, A. A. & HOLMES, E. C. (1993). Sequence variability in the 5' non coding region of hepatitis C virus: identification of a new virus type and restrictions on sequence diversity. Journal of General Virology 74, 661-668.

SIMMONDS, P., HOLMES, E. C., CHA, T. A., CHAN, S. W., McOMISH, F., IRVINE, B., BEALL, E., YAP, P. L., KOLBERG, J. and URDEA, M. S. (1993) Classification of hepatitis C virus into six major genotypes and a series of subtypes by phylogenetic analysis of the NS-5 region. Journal of General Virology 74, 2391-2399.

SIMMONDS, P., BALFE, P., LUDLUM, C. A., BISHOP, J. 0. and BROWN, A. J. (1990) Analysis of sequence diversity in hypervariable regions of the external glycoprotein of human immunodeficiency virus type 1. Journal of Virology 64, 5840-5850.

SIMMONDS, P., and CHAN, S. W., (1993) Analysis of viral sequence variation by PCR. In Molecular Virology: A Practical Approach, pp. 109-138. Edited by A. J. Davidson and R. M. Elliot. Oxford IRL Press.

SIMMONDS, P., ROSE, K. A., GRAHAM, S., CHAN, S. W., McOMISH, F., DOW, B. C., FOLLETT, E. A. C., YAP, P. L., and MARSDEN, H., J. Clin. Microb. 31: 1493.

TAKADA, N., TAKASE, S. ENOMOTO, N., TAKADA, A. & DATE, T. (1992). Clinical backgrounds of the patients having different types of hepatitis C virus genomes. J.Hepatol. 14, 35-40.

TAKAMIZAWA, A., MORI, C., FUKE, I., MANABE, S., MURAKAMI, S., FUJITA, J., ONISHI, E., ANDOH, T., YOSHIDA, I & OKAYAMA, H. (1991). Structure and organisation of the hepatitis C virus genome isolated from human carriers. Journal of Virology 65, 1105-1113.

TANAKA, T., KATO, N., NAKAGAWA, M., OOTSUYAMA, Y., CHO, M. J., NAKAZAWA, T., HUIKATA, M., ISHIMURA, Y. & SHIMOTOHNO, K. (1992). Molecular cloning of hepatitis C virus genome from a single Japanese carrier: sequence variation within the same individual and among infected individuals. Virus Tes. 23, 39-53.

WEINER, A. J., BRAUER, M. J., ROSENBLATT, J., RICHMAN, K. H., TUNG, J., CRAWFORD, K., BONINO, F., SARACCO, G., CHOO, Q. L., HOUGHTON, M & ET AL. (1991). Variable and hypervariable domains are found in the regions of HCV corresponding to the flavivirus envelope and NS 1 proteins and the pestivirus envelope glycoproteins. Virology 180, 842-848.

YANISCH-PERRON, C., VIEIRA, J. and MESSING, J. (1985) Improved M13 phage cloning vectors and host strains: nucleotide sequences of the M13mp18 and pUC19 vectors. Gene 33, 103-107.

YOSHIOKA, K., KAKUMU, S., WAKITA, T., ISHIKAWA, T., ITOH, Y., TAKAYANAGI, M., HIGASHI, Y., SHIBATA, M. & MORISHIMA, T. (1992). Detection of hepatitis C virus by polymerase chain reaction and response to interferon-alpha therapy: relationship to genotypes of hepatitis C virus. Hepatology 16, 293-299.

That which is claimed:

1. An isolated polynucleotide sequence comprising a nucleotide sequence selected from the group consisting of:

a) the nucleotide sequence of SEQ ID NO:49; and b) a nucleotide sequence encoding the amino acid sequence of SEQ ID NO:50.

* * * * *